US012642256B2

(12) United States Patent (10) Patent No.: US 12,642,256 B2
Lee et al. (45) Date of Patent: Jun. 2, 2026

(54) HEMOPHILIA B RAT MODEL

(71) Applicant: TOOLGEN INCORPORATED, Seoul (KR)

(72) Inventors: Jae Young Lee, Seoul (KR); Hee Sook Bae, Gyeonggi-do (KR); Hye Jung Shin, Seoul (KR); Dong Woo Song, Seoul (KR); Un Gi Kim, Seoul (KR); Kyu Jun Lee, Seoul (KR)

(73) Assignee: TOOLGEN INCORPORATED, Seoul (KR)

( * ) Notice: Subject to any disclaimer, the term of this patent is extended or adjusted under 35 U.S.C. 154(b) by 1169 days.

(21) Appl. No.: 17/440,350

(22) PCT Filed: Mar. 24, 2020

(86) PCT No.: PCT/KR2020/004008
§ 371 (c)(1),
(2) Date: Sep. 17, 2021

(87) PCT Pub. No.: WO2020/197242
PCT Pub. Date: Oct. 1, 2020

(65) Prior Publication Data
US 2022/0192163 A1 Jun. 23, 2022

(30) Foreign Application Priority Data
Mar. 26, 2019 (KR) ........................ 10-2019-0034308

(51) Int. Cl.
| | |
|---|---|
| *A01K 67/027* | (2006.01) |
| *C12N 9/64* | (2006.01) |
| *C12N 15/10* | (2006.01) |
| *C12N 15/113* | (2010.01) |
| *C12N 15/85* | (2006.01) |
| *C12N 15/90* | (2006.01) |
| *C12N 9/22* | (2006.01) |

(52) U.S. Cl.
CPC ............ *A01K 67/027* (2013.01); *C12N 9/644* (2013.01); *C12N 15/10* (2013.01); *C12N 15/113* (2013.01); *C12N 15/85* (2013.01); *C12N 15/90* (2013.01); *C12N 9/22* (2013.01); *C12N 2310/20* (2017.05); *C12Y 304/21022* (2013.01)

(58) Field of Classification Search
CPC ...... A01K 67/027; C12N 9/644; C12N 15/10; C12N 15/113; C12N 15/85
See application file for complete search history.

(56) References Cited

U.S. PATENT DOCUMENTS

| | | | |
|---|---|---|---|
| 6,479,626 | B1 | 11/2002 | Kim et al. |
| 6,903,185 | B2 | 6/2005 | Kim et al. |
| 7,153,949 | B2 | 12/2006 | Kim et al. |

| | | | |
|---|---|---|---|
| 2005/0064474 | A1 | 3/2005 | Urnov et al. |
| 2006/0188987 | A1 | 8/2006 | Guschin et al. |
| 2013/0217131 | A1 | 8/2013 | Kim et al. |

FOREIGN PATENT DOCUMENTS

| | | |
|---|---|---|
| JP | 2011-229456 A | 11/2011 |
| KR | 10-2018-0018457 A | 2/2018 |
| WO | WO 2009/088876 A2 | 7/2009 |
| WO | WO 2012/093833 A2 | 7/2012 |

OTHER PUBLICATIONS

Great Lakes Hemophilia Foundation, https://glhf.org/resources/facts-about-bleeding-disorders/types-of-bleeding-disorders/ (Year: 2025).*
Rallapalli, et al., International Society on Thrombosis and Haemostasis (2013) 11: 1329-1340 (Year: 2013).*
Liu et al Blood (2023) 141(6): 677-680 (Year: 2023).*
GeneCards—retrieved from internet Jul. 14, 2025 https://www.genecards.org/cgi-bin/carddisp.pl?gene=F9&keywords=factor,ix (Year: 2025).*
Office action issued on May 8, 2023 from Japan Intellectual Property Office in a counterpart Japanese Patent Application No. 2021-560162 (English translation is also submitted herewith.).
Database GenBank [online], Accession. NM_031540, Feb. 22, 2019 <URL:https://www.ncbi.nlm.nih.gov/nuccore/281604081?sat=47&satkey=42801687>.
Wang L et al., "A factor IX-deficient mouse model for hemophilia B gene therapy", Proceedings of the national academy of sciences, vol. 94, No. 21, Oct. 1, 1997, pp. 11563-11566.
Sabatino Denise E et al., "Novel hemophilia B mouse models exhibiting a range of mutations in the Factor IX gene", Blood, American Society of Hematology, vol. 104, No. 9, Nov. 1, 2004, pp. 2767-2774.
Jin Da-Yun et al., "Creation of a mouse expressing defective human factor IX", Blood, American Society of Hematology, vol. 104, No. 6, 2004, pp. 1733-1739.
Database Biosis (Online) Biosciences information service, Philadelphia, PA, UA Nov. 2015.
Nielsen L. N. et al., "A novel F8 -/- rat as a translational model of human hemophilia A", Journal of thrombosis and Haemostasis, vol. 12, No. 8, Aug. 1, 2014, pp. 1274-1282.
Metzger J M, et al., "Titrating haemophilia B phenotypes using siRNA strategy: evidence that antithrombotic activity is separated from bleeding liability" Thrombosis and Haemostasis, 2015 vol. 113(6), pp. 1300-1311.
International Search Report for PCT/KR2020/004008 mailed on Jun. 30, 2020.
Y'En, C.-T. et al. "Current animal models of hemophilia: the state of the art", Thrombosis Journal. 2016, vol. 14, thesis No. 22, pp. 101-106.

(Continued)

*Primary Examiner* — Evelyn Y Pyla
*Assistant Examiner* — Katherine R Small
(74) *Attorney, Agent, or Firm* — The PL Law Group, PLLC

(57) ABSTRACT

The present invention relates to a hemophilia B rat and a method of producing the hemophilia B rat. More particularly, the present invention relates to a hemophilia B rat having F9 factor knocked-down or knocked-out and a method of producing the hemophilia B rat.

1 Claim, 8 Drawing Sheets

Specification includes a Sequence Listing.

(56) References Cited

OTHER PUBLICATIONS

Lozie, J. N. et al. "Animal Models of Hemophilia and Related Bleeding Disorders", Seminars in Hematology. 2013, vol. 50, No. 2, pp. 175-184.

Sabatino. D. E. et al. "Animal Models of Hemophilia", Prog. Mol. Biol. Transl. Sci. 2012, vol. 105, pp. 151-209, NIH Public Access Author Manuscript Version inner pp. 1-49.

Roger R.Beerli. et al. "Engineering polydactyl zinc-finger transcription factors", Nature Biotechnology 20, 135-141, Feb. 1, 2002 (English abstract is submitted herewith.).

C O Pabo. et al. "Design and selection of novel Cys2His2 zinc finger proteins", Annual Review Biochemistry, 2001, vol. 70, pp. 313-340 (English abstract is submitted herewith.).

M Isalan. et al. "A rapid, generally applicable method to engineer zinc fingers illustrated by targeting the HIV-1 promoter", Nature Biotechnology 19, 656-60, Jul. 2001 English abstract is submitted herewith.).

David J Segal. et al. "Custom DNA-binding proteins come of age: polydactyl zinc-finger proteins", Current Opinion in Biotechnology 2001, 12:632-637.

Y Choo. et al. "Advances in zinc finger engineering", Current Opinion in Biotechnology 2000, vol. 10(4); 411-416 (English abstract is submitted herewith.).

Jeongbin Park. et al. "Cas-Designer: a web-based tool for choice of CRISPR-Cas9 target sites", Oxford Bioinformatics, 31(24), 2015, 4014-4016.

* cited by examiner

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Rat_F9_Exon1_gRNA1_target DNA

<400> SEQUENCE: 1
gccatcatgg cagacgctcc                                              20

<210> SEQ ID NO 2
<211> LENGTH: 20
<212> TYPE: DNA
<213> ORGANISM: Artificial Sequence
<220> FEATURE:
<223> OTHER INFORMATION: Rat_F9_Exon1_gRNA2_target DNA

<400> SEQUENCE: 2
tgctgagtag atagcccaga                                              20

<210> SEQ ID NO 3
<211> LENGTH: 20
<212> TYPE: DNA
<213> ORGANISM: Artificial Sequence
<220> FEATURE:
<223> OTHER INFORMATION: Rat_F9_Exon2_gRNA3_target DNA

<400> SEQUENCE: 3
tggacgggta agaattttgg                                              20

<210> SEQ ID NO 4
<211> LENGTH: 20
<212> TYPE: DNA
<213> ORGANISM: Artificial Sequence
<220> FEATURE:
<223> OTHER INFORMATION: Rat_F9_Exon2_gRNA4_target DNA

<400> SEQUENCE: 4
ctttggacgg gtaagaattt                                              20

<210> SEQ ID NO 5
<211> LENGTH: 20
```

```
<212> TYPE: DNA
<213> ORGANISM: Artificial Sequence
<220> FEATURE:
<223> OTHER INFORMATION: Rat_F9_Exon2_gRNA5_target DNA

<400> SEQUENCE: 5
tgagttatat ctctttggac                                                    20

<210> SEQ ID NO 6
<211> LENGTH: 20
<212> TYPE: DNA
<213> ORGANISM: Artificial Sequence
<220> FEATURE:
<223> OTHER INFORMATION: Rat_F9_Exon2_gRNA6_target DNA

<400> SEQUENCE: 6
cgtccaaaga gatataactc                                                    20

<210> SEQ ID NO 7
<211> LENGTH: 20
<212> TYPE: DNA
<213> ORGANISM: Artificial Sequence
<220> FEATURE:
<223> OTHER INFORMATION: Rat-F9_exon1_F

<400> SEQUENCE: 7
ctttcctgac agcagcacaa                                                    20

<210> SEQ ID NO 8
<211> LENGTH: 20
<212> TYPE: DNA
<213> ORGANISM: Artificial Sequence
<220> FEATURE:
<223> OTHER INFORMATION: Rat-F9_exon1_R

<400> SEQUENCE: 8
atgcaccgca aacactgtaa                                                    20

<210> SEQ ID NO 9
<211> LENGTH: 20
<212> TYPE: DNA
<213> ORGANISM: Artificial Sequence
<220> FEATURE:
<223> OTHER INFORMATION: Rat-F9_exon2_F

<400> SEQUENCE: 9
agggaatgac gatcaccttg                                                    20

<210> SEQ ID NO 10
<211> LENGTH: 21
<212> TYPE: DNA
<213> ORGANISM: Artificial Sequence
<220> FEATURE:
<223> OTHER INFORMATION: Rat-F9_exon2_R

<400> SEQUENCE: 10
ttgacgtttt ccatcttttg c                                                  21

<210> SEQ ID NO 11
<211> LENGTH: 54
<212> TYPE: DNA
<213> ORGANISM: Artificial Sequence
<220> FEATURE:
<223> OTHER INFORMATION: Rat_F9_exon1_2nd_F

<400> SEQUENCE: 11
```
acactctttc cctacacgac gctcttccga tctcccattc agcttgtact ttgg          54

<210> SEQ ID NO 12
<211> LENGTH: 54
<212> TYPE: DNA
<213> ORGANISM: Artificial Sequence
<220> FEATURE:
<223> OTHER INFORMATION: Rat_F9_exon1_2nd_R

<400> SEQUENCE: 12
gtgactggag ttcagacgtg tgctcttccg atctgacatg ctgcctgcta caat          54

<210> SEQ ID NO 13
<211> LENGTH: 57
<212> TYPE: DNA
<213> ORGANISM: Artificial Sequence
<220> FEATURE:
<223> OTHER INFORMATION: Rat_F9_exon2_2nd_F

<400> SEQUENCE: 13
acactctttc cctacacgac gctcttccga tctcccaaag agaaattagc tatggaa       57

<210> SEQ ID NO 14
<211> LENGTH: 54
<212> TYPE: DNA
<213> ORGANISM: Artificial Sequence
<220> FEATURE:
<223> OTHER INFORMATION: Rat_F9_exon2_2nd_R

<400> SEQUENCE: 14
gtgactggag ttcagacgtg tgctcttccg atcttcgtgc ttcttcaaaa ctgc          54

<210> SEQ ID NO 15
<211> LENGTH: 63
<212> TYPE: DNA
<213> ORGANISM: Artificial Sequence
<220> FEATURE:
<223> OTHER INFORMATION: Rat_F9_Exon1_gRNA1_synthesis seq

<400> SEQUENCE: 15
gaaattaata cgactcacta taggccatca tggcagacgc tccgttttag agctagaaat    60
agc                                                                  63

<210> SEQ ID NO 16
<211> LENGTH: 63
<212> TYPE: DNA
<213> ORGANISM: Artificial Sequence
<220> FEATURE:
<223> OTHER INFORMATION: Rat_F9_Exon1_gRNA2_ synthesis seq

<400> SEQUENCE: 16
gaaattaata cgactcacta tagtgctgag tagatagccc agagtttttag agctagaaat   60 agc                                                                  63

<210> SEQ ID NO 17
<211> LENGTH: 63
<212> TYPE: DNA
<213> ORGANISM: Artificial Sequence
<220> FEATURE:
<223> OTHER INFORMATION: Rat_F9_Exon2_gRNA3_ synthesis seq

<400> SEQUENCE: 17
gaaattaata cgactcacta tagtggacgg gtaagaattt tgggtttttag agctagaaat   60 agc                                                                  63

-continued

```
<210> SEQ ID NO 18
<211> LENGTH: 63
<212> TYPE: DNA
<213> ORGANISM: Artificial Sequence
<220> FEATURE:
<223> OTHER INFORMATION: Rat_F9_Exon2_gRNA4_ synthesis seq

<400> SEQUENCE: 18
gaaattaata cgactcacta tagctttgga cgggtaagaa tttgtttag agctagaaat      60 agc                                                                   63

<210> SEQ ID NO 19
<211> LENGTH: 63
<212> TYPE: DNA
<213> ORGANISM: Artificial Sequence
<220> FEATURE:
<223> OTHER INFORMATION: Rat_F9_Exon2_gRNA5_ synthesis seq

<400> SEQUENCE: 19
gaaattaata cgactcacta tagtgagtta tatctctttg gacgttttag agctagaaat      60
agc                                                                   63

<210> SEQ ID NO 20
<211> LENGTH: 63
<212> TYPE: DNA
<213> ORGANISM: Artificial Sequence
<220> FEATURE:
<223> OTHER INFORMATION: Rat_F9_Exon2_gRNA6_ synthesis seq

<400> SEQUENCE: 20
gaaattaata cgactcacta tagcgtccaa agagatataa ctcgttttag agctagaaat      60
agc                                                                   63

<210> SEQ ID NO 21
<211> LENGTH: 96
<212> TYPE: RNA
<213> ORGANISM: Artificial Sequence
<220> FEATURE:
<223> OTHER INFORMATION: Rat_F9_Exon1_gRNA1_target spCas9 sgRNA

<400> SEQUENCE: 21
gccaucaugg cagacgcucc guuuuagagc uagaaauagc aaguuaaaau aaggcuaguc      60
cguuaucaac uugaaaaagu ggcaccgagu cggugc                                96

<210> SEQ ID NO 22
<211> LENGTH: 96
<212> TYPE: RNA
<213> ORGANISM: Artificial Sequence
<220> FEATURE:
<223> OTHER INFORMATION: Rat_F9_Exon1_gRNA2_target spCas9 sgRNA

<400> SEQUENCE: 22
ugcugaguag auagcccaga guuuuagagc uagaaauagc aaguuaaaau aaggcuaguc      60
cguuaucaac uugaaaaagu ggcaccgagu cggugc                                96

<210> SEQ ID NO 23
<211> LENGTH: 96
<212> TYPE: RNA
<213> ORGANISM: Artificial Sequence
<220> FEATURE:
<223> OTHER INFORMATION: Rat_F9_Exon2_gRNA3_target spCas9 sgRNA
```

-continued

<400> SEQUENCE: 23
uggacgggua agaauuuugg guuuuagagc uagaaauagc aaguuaaaau aaggcuaguc     60
cguuaucaac uugaaaaagu ggcaccgagu cggugc                              96

<210> SEQ ID NO 24
<211> LENGTH: 96
<212> TYPE: RNA
<213> ORGANISM: Artificial Sequence
<220> FEATURE:
<223> OTHER INFORMATION: Rat_F9_Exon2_gRNA4_target spCas9 sgRNA

<400> SEQUENCE: 24
cuuuggacgg guaagaauuu guuuuagagc uagaaauagc aaguuaaaau aaggcuaguc     60
cguuaucaac uugaaaaagu ggcaccgagu cggugc                              96

<210> SEQ ID NO 25
<211> LENGTH: 96
<212> TYPE: RNA
<213> ORGANISM: Artificial Sequence
<220> FEATURE:
<223> OTHER INFORMATION: Rat_F9_Exon2_gRNA5_target spCas9 sgRNA

<400> SEQUENCE: 25
ugaguuauau cucuuuggac guuuuagagc uagaaauagc aaguuaaaau aaggcuaguc     60
cguuaucaac uugaaaaagu ggcaccgagu cggugc                              96

<210> SEQ ID NO 26
<211> LENGTH: 96
<212> TYPE: RNA
<213> ORGANISM: Artificial Sequence
<220> FEATURE:
<223> OTHER INFORMATION: Rat_F9_Exon2_gRNA6_target spCas9 sgRNA

<400> SEQUENCE: 26
cguccaaaga gauauaacuc guuuuagagc uagaaauagc aaguuaaaau aaggcuaguc     60
cguuaucaac uugaaaaagu ggcaccgagu cggugc                              96

<210> SEQ ID NO 27
<211> LENGTH: 76
<212> TYPE: RNA
<213> ORGANISM: Artificial Sequence
<220> FEATURE:
<223> OTHER INFORMATION: spCas9 sgRNA tail sequence

<400> SEQUENCE: 27
guuuuagagc uagaaauagc aaguuaaaau aaggcuaguc cguuaucaac uugaaaaagu     60
ggcaccgagu cggugc                                                    76

<210> SEQ ID NO 28
<211> LENGTH: 77
<212> TYPE: RNA
<213> ORGANISM: Artificial Sequence
<220> FEATURE:
<223> OTHER INFORMATION: cjCas9 sgRNA tail sequence

<400> SEQUENCE: 28
guuuuagucc cugaaaaggg acuaaaauaa agaguuugcg ggacucugcg ggguuacaau     60
ccccuaaaac cgcuuuu                                                   77

<210> SEQ ID NO 29
<211> LENGTH: 66

-continued

```
<212> TYPE: DNA
<213> ORGANISM: Artificial Sequence
<220> FEATURE:
<223> OTHER INFORMATION: primer

<400> SEQUENCE: 29
gaaattaata cgactcacta tagcgtccaa agagatataa ctcagggttt tagagctaga     60
aatagc                                                                66

<210> SEQ ID NO 30
<211> LENGTH: 83
<212> TYPE: DNA
<213> ORGANISM: Artificial Sequence
<220> FEATURE:
<223> OTHER INFORMATION: primer

<400> SEQUENCE: 30
aaaaaaagca ccgactcggt gccacttttt caagttgata acggactagc cttattttaa     60
cttgctattt ctagctctaa aac                                             83

<210> SEQ ID NO 31
<211> LENGTH: 110
<212> TYPE: DNA
<213> ORGANISM: Rattus norvegicus

<400> SEQUENCE: 31
actttcaaat ttcagttttt cttgatcgcg aaaatgcacc aaaattctta cccgtccaaa     60
gagatataac tcagggaaac tggaagagtt tgttcaggga aaccttgaga               110

<210> SEQ ID NO 32
<211> LENGTH: 108
<212> TYPE: DNA
<213> ORGANISM: Artificial Sequence
<220> FEATURE:
<223> OTHER INFORMATION: indel in Exon 2 region of F9 gene

<400> SEQUENCE: 32
actttcaaat ttcagttttt cttgatcgcg aaaatgcacc aaaattctta cccgtccaaa     60
gagatatatc agggaaactg gaagagtttg ttcagggaaa ccttgaga                 108

<210> SEQ ID NO 33
<211> LENGTH: 75
<212> TYPE: DNA
<213> ORGANISM: Artificial Sequence
<220> FEATURE:
<223> OTHER INFORMATION: indel in Exon 2 region of F9 gene

<400> SEQUENCE: 33
actttcaaat ttcagttttt cttgatcgcg aaaatgcagg gaaactggaa gagtttgttc     60
agggaaacct tgaga                                                      75

<210> SEQ ID NO 34
<211> LENGTH: 106
<212> TYPE: DNA
<213> ORGANISM: Artificial Sequence
<220> FEATURE:
<223> OTHER INFORMATION: indel in Exon 2 region of F9 gene

<400> SEQUENCE: 34
actttcaaat ttcagttttt cttgatcgcg aaaatgcacc aaaattctta cccgtccaaa     60
gagatatcag ggaaactgga agagtttgtt cagggaaacc ttgaga                   106
```

-continued

```
<210> SEQ ID NO 35
<211> LENGTH: 115
<212> TYPE: DNA
<213> ORGANISM: Artificial Sequence
<220> FEATURE:
<223> OTHER INFORMATION: indel in Exon 2 region of F9 gene

<400> SEQUENCE: 35
actttcaaat ttcagttttt cttgatcgcg aaaatgcacc aaaattctta cccgtccaaa       60
gagatataac aacaatcagg gaaactggaa gagtttgttc agggaaacct tgaga          115

<210> SEQ ID NO 36
<211> LENGTH: 56
<212> TYPE: DNA
<213> ORGANISM: Artificial Sequence
<220> FEATURE:
<223> OTHER INFORMATION: primer

<400> SEQUENCE: 36
acactctttc cctacacgac gctcttccga tctcgtccaa agagatataa ctcagg          56
```

HEMOPHILIA B RAT MODEL

REFERENCE TO AN ELECTRONIC SEQUENCE LISTING

A sequence listing electronically submitted with the present application on Sep. 17, 2021 as an ASCII text file named 20210917_Q61521GR14_TU_SEQ, created on Sep. 17, 2021 and having a size of 9,000 bytes, is incorporated herein by reference in its entirety.

BACKGROUND

1. Technical Field

The present invention relates to a hemophilia B rat and a method of producing the same, and more particularly, a hemophilia B rat having F9 factor knocked down or knocked out and a method of producing the same.

2. Background Art

Hemophilia B, or Christmas disease, is a hereditary X-linked recessive hemorrhagic disorder caused by a defective blood clotting factor IX (F9). In cases of hemophilia B, not only the continuous bleeding occurs in a wound but also the spontaneous bleeding occurs in joints or muscles, and thus an incidence of complications like hemophilic arthropathy is also becoming a serious issue. Under the circumstances, development of a new therapy, which is both fundamental and effective, is needed and, for the evaluation of drug efficacy and safety, development of a more improved animal model is also required presently.

As a conventional hemophilia B animal model, mice have a problem that the phenomenon of spontaneous bleeding hardly occurs in tissues like joints and muscles (see, Yen C. T., Fan M.-N., Yang Y.-L., Chou S.-C., Yu I.-S., Lin S.-W. Thromb. J. 2016; 14:22) and those hemophilia B mice are not suitable for a use in the development and production of pharmaceutical products. Accordingly, there has been a demand for an animal model which is, as a hemophilia B animal model, more genetically similar to humans and expresses well the disease symptoms of hemophilia B. In addition, in biomedical field, there is an increasing demand for use of an animal model for accurate study of hemophilia B at relatively low cost.

In view of the above, the present invention provides a F9 factor-deficient rat as a hemophilia B disease model. With the rat animal model, symptoms of hemophilia B, more particularly, the phenomenon of spontaneous bleeding can be shown at sufficient level, and it may provide an important tool for developing therapeutic agents in future.

SUMMARY

The present application provides a hemophilia B rat and a method of producing the hemophilia B rat.

The present application also provides a composition comprising a genetic engineering technology capable of artificial engineering of the F9 gene for producing a hemophilia B rat.

The present application also provides a various uses using the hemophilia B rat.

To solve the above problems, the present application provides a hemophilia B rat as a hemophilia B animal model.

One embodiment disclosed in the present application relates to a hemophilia B rat having an artificial modification occurred in the genome.

The hemophilia B rat having an artificial modification occurred in the genome includes F9 gene in which a part or all in F9 gene is artificially engineered and/or modified.

In one embodiment, the artificially engineered F9 gene includes an artificial modification in an exon, an intron, a regulatory region, a 5' terminus or an adjacent region thereof, a 3' terminus or an adjacent region thereof, a splicing site, or the like.

The nucleotide sequence modification of F9 gene includes an addition, a deletion, or a substitution of one more nucleotides in the genome, but it is not limited thereto.

It may include;
an insertion of one or more nucleotides in the nucleotide sequence in F9 gene,
a deletion of one or more nucleotides in the nucleotide sequence in F9 gene,
a substitution of one or more nucleotides in the nucleotide sequence in F9 gene,
knock-down of the nucleotide sequence in F9 gene or a region of the F9 gene, or the like.

The artificial modification in genome can cause a mutation of F9 factor. Namely, a hemophilia B rat may include artificially modified F9 factor.

The artificially modified F9 factor includes an alteration and/or a substitution of one or more amino acid sequences.

For example, the amino acid can be altered to an amino acid with similar properties. Alternatively, the amino acid can be altered to an amino acid with different properties.

Protein expression level can be regulated by the alteration and/or the substitution of an amino acid.

Alternatively, protein structure and function can be affected by the alteration and/or the substitution of an amino acid.

Accordingly, as a result of the artificial modification of F9 factor, the hemophilia B rat cannot express the F9 factor at all or has the F9 factor with reduced expression level. Else, the rat has F9 factor with hypofunction or lost function.

One embodiment disclosed in the present application relates to a cell including artificially modified F9 factor and/or a gene encoding the artificially modified F9 factor.

The cell can be a transformed stem cell, a transformed embryonic cell, or a transformed somatic cell.

The transformed cell includes artificially modified F9 gene.

In one example, the transformed cell may include a gene having an addition, a deletion, or a substitution of nucleotide occurred in one or more regions in F9 gene.

In another example, the transformed cell can be a cell having the F9 gene knocked down and/or knocked out.

The transformed cell may include a genetic engineering technology for targeting F9 factor, i.e., engineered nuclease, antisense RNA, dominant negative mutant F9, ribozyme, or the like.

For example, the transformed cell includes CRISPR-Cas system, ZFN, TALEN or meganuclease, or a nucleic acid encoding them.

Alternatively, the transformed cell includes small interfering RNA (siRNA), short hairpin RNA (shRNA), or microRNA, or a nucleic acid encoding them, for example.

Alternatively, the transformed cell includes dominant negative mutant F9 targeting F9 factor or a ribozyme against nucleic acid encoding F9 factor, or a nucleic acid encoding them.

In a cell, the genetic engineering technology is included in various forms. For example, it can be in form of a vector which includes a nucleic acid encoding the genetic engineering technology.

The transformed cell can be either a cell in which F9 factor is not present at all or in which the expression level of F9 factor is reduced.

The transformed cell can be a cell in which the F9 factor has lost function or hypofunction.

The transformed cell can be a cell deficient of F9 factor.

The transformed cell may form a cell colony. The cell colony can be a single cell cultured from single cell.

One embodiment of the present application relates to a rat having artificially modified F9 factor.

Namely, it relates to a rat with down-regulated or lost expression or function of F9 factor as F9 gene is either knocked down or knocked out. Hereinbelow, the rat can be described interchangeably with an expression 'artificially modified rat'.

The artificially modified rat may exhibit a bleeding symptom (continuous bleeding or spontaneous bleeding).

The artificially modified rat may exhibit spontaneous bleeding and/or external bleeding.

According to one embodiment, the artificially modified rat has spontaneous bleeding in tissues.

It includes:

inflammation due to the spontaneous bleeding in tissues; and/or swelling due to the spontaneous bleeding in tissues.

The tissues can be a joint, a muscle, or an eye, for example.

The present specification provides a F9 gene genetic engineering technology for artificially engineering F9 gene.

The genetic engineering technology for causing an artificial modification in F9 gene is at least one selected from a technology of using engineered nuclease, a technology of using antisense RNA, and a technology of using a mutant gene or protein, but the genetic engineering technology is not limited to them.

The F9 gene genetic engineering technology disclosed in the present application can be one or more technology selected from the group consisting of CRISRP-Cas system as an engineered nuclease, ZFN, TALEN, and mega-nuclease.

The engineered nuclease may form a complementary bond with a nucleotide sequence of a whole or partial sequence of F9 gene.

The engineered nuclease may artificially modify F9 gene by removing the whole F9 gene, by deleting or substituting a partial nucleotide sequence in F9 gene, or by inserting an exogenous nucleotide.

The engineered nuclease may artificially modify F9 gene by forming a complementary bond with a partial nucleotide sequence, in F9 gene, of an exon region, an intron region, a regulatory region, a splicing site, a 5' terminus or an adjacent region thereof or a 3' terminus or an adjacent region thereof.

The F9 gene genetic engineering technology disclosed in the present application relates to an antisense RNA technology involving complementary binding to F9 gene.

The genetic engineering technology using an antisense RNA can be one or more technology of small interfering RNA (hereinbelow, referred to as 'siRNA'), short hairpin RNA (hereinbelow, referred to as 'shRNA'), and microRNA (hereinbelow, referred to as 'miRNA').

The antisense RNA may form a complementary bond with a partial nucleotide sequence of F9 gene and it may regulate the protein expression of F9 gene.

For example, the antisense RNA may form a complementary bond with the nucleotide sequence, in F9 gene, of an exon region, an intron region, a regulatory region, a splicing site, a 5' terminus or an adjacent region thereof, or a 3' terminus or an adjacent region thereof in F9 gene.

The present application also provides a dominant negative mutant, a ribozyme, an intracellular antibody, a peptide or small molecule for regulating the function and expression of F9 factor.

The present specification provides a composition for engineering F9 gene to produce a hemophilia B rat model including the followings: a guide RNA or a DNA encoding the guide RNA; and an editor protein or a DNA encoding the editor protein. Herein, the guide RNA has a sequence that is selected from the group consisting of SEQ ID NOs: 21 to 26, and the guide RNA is characterized by targeting a whole or partial sequence of F9 gene as a target sequence. It is also characterized in that the editor protein includes Cas9 protein originating from *Streptococcus pyogenes* and the guide RNA and the editor protein can cause an artificial modification in F9 gene by forming a guide RNA-editor protein complex.

In one embodiment, the guide RNA and the editor protein can be present in form of RNP (ribonucleoprotein) in which they form a complex.

In one embodiment, a DNA encoding the guide RNA and a DNA encoding the editor protein can be present in form of a vector.

The present specification provides a guide RNA having a sequence selected from the group consisting of SEQ ID NOs: 21 to 26.

The present specification provides a composition for producing a hemophilia B rat model.

One embodiment of the context disclosed by the present application relates to a composition for engineering or modifying F9 gene.

The composition for engineering or modifying F9 gene may include the aforementioned the engineered nuclease or a nucleic acid encoding the engineered nuclease. For example, the engineered nuclease can be one or more nuclease of TALEN, ZFN, meganuclease, and CRISPR-enzyme.

In one example, the composition for engineering F9 gene may include a guide RNA capable of forming a complementary bond with partial nucleotide sequence in F9 gene and Cas9 enzyme, or a complex thereof.

In another example, the composition for engineering F9 gene may include an antisense RNA capable of forming a complementary bond with partial nucleotide sequence in F9 gene, e.g., siRNA, shRNA, or the like.

In still another example, the composition for engineering F9 gene may include a dominant negative mutant F9 factor, a ribozyme, or the like.

The composition may include, as a mixture, one or more components of one or more guide RNA and Cas9 enzyme or a complex thereof; one or more of antisense RNA; or a dominant negative mutant F9 factor.

The composition can be provided in form of an expression cassette.

In the composition, the F9 gene genetic engineering technology is included in form of a viral vector, a non-viral vector, or a non-vector.

In one example, the composition includes the F9 gene genetic engineering technology in form of RNP (ribonucleoprotein).

In another example, the composition includes a recombinant expression vector including the F9 gene genetic engineering technology.

The present specification provides a method of producing a hemophilia B rat.

One embodiment of the present application includes a step of delivering the genetic engineering technology to an inside of rat cell for artificial modification of F9 gene.

Herein, the F9 gene genetic engineering technology can be delivered by using a naked nucleic acid vector, a non-viral vector, or a viral vector.

In one embodiment, to produce an artificially modified rat, a step of introducing the F9 gene genetic engineering technology by using a non-viral vector to rat cell can be included.

For example, when the F9 gene genetic engineering technology is a technology using a guide RNA and Cas9, the guide RNA-Cas9 complex can be delivered to an inside of a cell by microinjection. Namely, the guide RNA and Cas9 can be delivered in form of a ribonucleoprotein (RNP). The guide RNA-Cas9 complex refers to a complex formed by an interaction between a guide RNA and CRISPR enzyme.

A rat-derived cell transformed with the recombinant expression vector for artificial modification of F9 gene can be multiplied and cultured according to a method well known in the art.

Another embodiment of the present application may include a step of selecting transformed cells including F9 gene-targeted genetic engineering technology.

Herein, the transformed cell can be selected from a colony by using one or more selection elements of antibiotic resistance gene, antigen-antibody reaction, fluorescent protein, and surface marker gene.

One embodiment disclosed in the present specification relates to a method of producing a F9 gene-engineered rat using transplanting embryonic cells.

The method may include:
(a) exposing embryonic cells isolated from tissues of a rat to an engineered nuclease (meganuclease, ZFN, TALEN and/or CRISPR-enzyme system);
(b) transplanting embryonic cells into a surrogate mother;
(c) forming artificially modified F9 gene by causing a modification in the cell chromosome based on specific binding of the engineered nuclease to F9 gene site in the embryonic cells; and
(d) allowing the surrogate mother to be pregnant with a rat including artificially modified F9 gene.

Details of a common technology for each step can be understood in view of conventional embryonic transplantation methods well known in the art.

One embodiment disclosed in the present specification relates to a method of producing a transformed rat for hemophilia B model which has F9 gene knocked out by artificial modification, said method including transplantation of a nucleus of a nuclear donor cell, which is introduced a recombinant vector, into a denucleated oocyte; and birth of a rat offspring, and it also relates to a rat as hemophilia B model produced by the method.

In a specific embodiment, a hemophilia B rat is produced according to a method of somatic cell nuclear transfer (SCNT) the method using a transformed cell line in which the F9 gene is knocked out by artificial modification.

The method for producing a hemophilia B rat may include:
(a) producing a nuclear donor cell including culturing somatic cells or stems cells isolated from tissues of a rat;

(b) introducing an artificial engineering nuclease targeting a part or all of F9 gene into the nuclear donor cell;
(c) producing a denucleated oocyte by removing a nucleus from rat oocyte,
(d) microinjecting the nuclear donor cell of the step (b) to the denucleated oocyte of the step (c), and fusing the nuclear donor cell with the denucleated oocyte;
(e) activating the fused oocyte which has been fused in the step (d); and
(f) transplanting the activated oocyte in an oviduct of a surrogate mother.

Details of a common technology for each step can be understood in view of conventional methods for producing cloned animals by using somatic cell nucleus transplant technology or the like that are well known in the art.

The present specification provides a method of producing a hemophilia B rat model including an artificial modification in F9 gene, the method including the followings: contacting a rat cell with a composition for F9 gene genetic engineering for producing a hemophilia B rat model thereby, an artificial modification is induced in F9 gene of the rat cell; and introducing the rat cell to a rat to produce a hemophilia B rat model.

In one embodiment, the contacting can be carried out by one or more methods selected from electroporation, liposome, plasmid, viral vector, nanoparticles, and PTD (protein translocation domain) fusion protein methods.

One embodiment provides a method for producing a transformed rat by using CRISPR/Cas9 system.

The method of producing a transformed rat by using CRISPR/Cas9 system may include:
(a) introducing CRISPR-enzyme system, targeting a part or all of the nucleic acids in F9 gene in a rat, into embryonic cells;
(b) transplanting embryonic cells into a surrogate mother;
(c) forming artificially modified F9 gene by causing a modification in the cell chromosome based on specific binding of the CRISPR-enzyme system to F9 gene site in the embryonic cells; and
(d) allowing the surrogate mother to be pregnant with a rat including the artificially modified F9 gene.

The present specification can provide an animal model for screening pharmaceuticals to treat hemophilia B by using a novel hemophilia B rat model which has not exist before. More particularly, the present specification can provide an animal model for screening pharmaceuticals to prevent or treat spontaneous bleeding of hemophilia B.

In one embodiment, the method for screening pharmaceuticals for hemophilia B may include steps of:
(a) administering a candidate material for palliating, preventing, or treating hemophilia B to a hemophilia B rat model; and
(b) comparing and analyzing the candidate material with a control group which has not been administered the candidate material, following administration of the candidate material.

The candidate material is preferably any one or more materials selected from the group consisting of a peptide, a protein, a non-peptide compound, a synthetic compound, a fermentation product, a cell extract, a plant extract, and an animal extract, but it is not limited thereto.

The compound can be either a novel compound or a compound already known in the art. Herein, the compound may form a salt.

According to the technologies that are disclosed in the present specification, the following effects can be obtained.

According to the technologies that are disclosed in the present specification, a hemophilia B rat can be provided. More particularly, a hemophilia B rat including artificially modified F9 factor is provided.

The hemophilia B rat provided according to the present specification is genetically similar to humans and useful for studying accurate causal mechanism of the disease, and also, as an optimum animal model for screening pharmaceuticals, it can be variously used for searching therapeutic agents for hemophilia B, development of a diagnostic method for hemophilia B or the like, and thus it would be very advantageously used as an animal model of hemophilia B.

BRIEF DESCRIPTION OF THE DRAWINGS

FIG. 1A is a graph in which aPTT (activated partial thromboplastin time) is analyzed by comparison between F9(+/+) rat and F9(−/−) rat.

FIG. 1B is a graph in which thrombin time is analyzed by comparison between F9(+/+) rat and F9(−/−) rat. FIG. 1C is a graph in which platelet count is analyzed by comparison between F9(+/+) rat and F9(−/−) rat.

FIG. 3A shows the transverse (cross-sectional) portion of the hindlimb showing the pain region of a F9 rat. The pain region was excised and subjected to hematoxylin and eosin (H&E) staining to determine the morphology of the pain region of a F9 rat. FIG. 3B shows a transverse (cross-sectional) view of said pain region.

FIG. 4A shows severe swelling and discoloration of the hindlimb joint associated with extensive spontaneous subcutaneous and intramuscular bleeding. FIG. 4B shows the same hindlimb with the skin removed, demonstrating extensive accumulation of blood (hematoma) within the muscle and periarticular tissue. FIG. 4C shows a direct comparison between the exposed hindlimb of the F9 knockout rat (C-1) and the wild-type rat hindlimb (C-2).

FIG. 7A shows marked swelling and discoloration of the scalp area, FIG. 7B shows hemorrhagic infiltration and edema localized to the lateral abdominal wall, FIG. 7C shows extensive bruising and swelling of the forelimb, and FIG. 7D shows periorbital swelling.

DETAILED DESCRIPTION

Figure 1A:
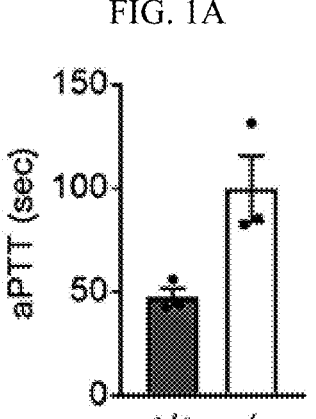
FIGS. 1A to 1C are graphs in which F9(+/+) rat and F9(−/−) rat are compared to each other for analysis.

Unless defined otherwise, all technical and scientific terms used in the present specification have the same meaning as those commonly understood by a person skilled in the art to which the present invention pertains. Although methods and materials that are identical or similar to those described in the present specification can be used for carrying out the present invention or a test of the present invention, suitable methods and materials are described in the followings. All publications, patent applications, patents, and other reference literatures referred to in the present specification are incorporated herein by reference in their entirety. In addition, the materials, methods, and examples are given only for exemplification and it is not intended to be limited by them.

Definition of Terminology

Transformation, Transformed Cell, and Transformed Animal

"Transformation (genetic modification)" refers to artificial modification of a polynucleotide of animal genome in a cell. The modification includes deletion or substitution of part of the polynucleotide included in animal genome in a cell, and also insertion of a nucleotide or a polynucleotide to animal genome.

As described herein, the term "transformation" includes addition, alteration, or removal of protein or RNA which can be expressed in a cell.

"Transformed cell" refers to a cell which includes a transformed region of animal genome in a cell.

"Transformed animal" refers to an animal including at least one transformed cell. Animal F0 may include a first transformed cell. The animal F0 may produce F1 progeny. At least one cell included in the F1 and subsequent generations following F1 may include an animal genome which includes region with the same nucleotide sequence as the transformed region in animal genome of the transformed cell. As described herein, the "transformed animal" includes the F0, F1, and subsequent generations following F1.

Animal Disease Model

"Animal disease model" refers to an animal having a disease that is very similar to human disease. For a study of human diseases, the usefulness of an animal disease model is based on physiological and genetic similarity between humans and animals. In a study of diseases, the biomedical animal disease model provides study materials regarding various causes, onset mechanisms, and diagnosis of disease, and, according to a study using an animal disease model, genes related to the disease can be found, interactions between genes can be understood, and basic data for determining the possibility of actual application can be obtained based on efficacy and toxicity test of a candidate drug material which has been developed.

Animal or Test Animal

"Animal" or "test animal" refers to any mammal except human, rodent, or the like. The animal includes animals at any age including embryo, fetus, newborn, and adult. The animals employed in the present specification can be obtained from a commercial source, for example. The animals include a test animal or other animals, rabbit, rodent (e.g., mouse, rat, hamster, *Gerbillus*, and guinea pig), cow, sheep, pig, goat, horse, dog, cat, bird (e.g., chicken, turkey, duck, and goose), and primates (e.g., chimpanzee, monkey, and rhesus monkey), but they are not limited thereto. The most preferred animal is a rat.

Engineered Nuclease

"Engineered nuclease" is a term which refers to an artificial nuclease capable of binding to a certain gene and causing, according to cleavage at specific locus of a nucleic acid, e.g., specific locus of DNA, a damage or a break, and/or a system including the nuclease. It is also referred to as "target-specific (endo) nuclease" or "genetic scissors". The engineered nuclease is a sequence-specific endonuclease. "Sequence-specific endonuclease" or "sequence-specific nuclease" refers to, unless specifically described otherwise, a protein recognizing and binding to a polynucleotide in specific nucleotide sequence, for example, a target gene, to catalyze a single- or double-strand break in the polynucleotide. As a specific sequence can be specifically recognized to cut off a nucleic acid, it is very useful for genome editing technology. Examples thereof include ZFN (zinc finger protein), TALEN (transcription activator-like effector protein), and RGEN (RNA-guided endonuclease) including CRISPR/Cas system.

CRISPR-Enzyme System

"CRISPR-enzyme system" refers to a complex comprising proteins that can interact with a target site on an animal genome in cell or a target site of an exo-polynucleotide to cut off a part of the target site.

CRISPR-enzyme system may comprise a guide nucleic acid and a CRISPR enzyme.

Knock-Out

"Knock-out" refers to a modification on a gene sequence to yield functional reduction of a target gene. And preferably, the expression of the target gene becomes undetectable or meaningless. In the present invention, F9 gene knock-out refers to the hypofunction of F9 gene and the gene is expressed at non-detectable or meaningless level. Knock-out transformant can be a transformed animal which has a heterozygous knock-out of F9 gene or a homozygous knock-out of F9 gene. For example, the knock-out includes exposing a subject animal to a material which enhances target gene modification, introducing an enzyme which enhances recombination at target gene site, or a conditional knock-out capable of target gene modification by directing or the like for target gene modification after birth.

Target Gene

"Target gene" refers to a nucleic acid encoding a polypeptide in cell, unless specifically described otherwise. "Target sequence" refers to part of a target gene, for example, the target sequence refers to at least one exon sequence of a target gene; an intron sequence or regulatory sequence of a target gene; or a combination of exon and intron sequences, intron and regulatory sequences, exon and regulatory sequences, or exon, intron, and regulatory sequences of a target gene, unless specifically described otherwise.

Culture

"Culture" refers to growing an organism or part of an organism (organ, tissue, cell, or the like) in an environment which has been suitably and artificially adjusted. For culture, temperature, humidity, light, composition of gas phase (partial pressure of carbon dioxide or oxygen), and the like are essential as an external condition. Other than those, a culture medium (or incubator) exhibits the most direct influence on an organism to be cultured. The culture medium is not only a direct environment for the organism but also a source of various nutrients that are required for survival or proliferation.

In Vitro Culture

"In vitro culture" refers to a series of experimental procedures of performing culture, in an incubator of a laboratory at an environmental condition similar to living body. The procedures are different from a method in which cells or the like grow in a living body.

Cells, Host Cells, and Modified Cells

"Cells", "host cells", "modified cells" and the like refer to not only specific subject cells but also a progeny (also referred offspring) of those cells or a potential progeny of those cells. Because a specific modification may occur at later generations due to the mutation or environmental effect, those progenies may not be actually the same as the parent cells, but they are still included by the terms and scope described in the present specification.

Modified or Engineered

The terms "modified" or "engineered" described in relation to a nucleic acid are used interchangeably in the present specification, and they refer to an artificial modifying to the nucleotide sequence constituting a gene. The modification may include deletion, substitution, insertion, inversion and the like in one or more nucleotides. Modified or engineered nucleotide sequence can be exhibited as an alteration of expression and/or functional activity of the nucleic acid or expression product thereof. For example, the alteration can be enhancement, promotion, reduction, loss or the like.

Nuclear Donor Cell

"Nuclear donor cell" refers to a cell or a cell nucleus which delivers a nucleus to a nuclear recipient oocyte as a nucleus acceptor. "Oocyte" preferably refers to a mature oocyte at metaphase of the meiosis II. In the present specification, a somatic cell or a stem cell of a rat can be used as the nuclear donor cell.

Somatic Cell

"Somatic cell" refers to a cell other than reproductive cells, among the cells constituting a multi-cellular organism. It includes differentiated cells specialized in certain purpose so as not to become other cells; and cells having a property of differentiating into cells with some other different functions.

Stem Cell

"Stem cell" refers to a cell capable of developing into any kind of tissues. The stem cell has two basic characteristics, i.e., self-renewal to produce itself by repeated division and multi-differentiation property allowing differentiation into cells with specific function depending on environment.

Nuclear Transfer

"Nuclear transfer" refers to, a technology of removing a nucleus from an oocyte, and introducing a donor nucleus obtained from another cell into the oocyte. More particularly, "nuclear transfer" includes a technology of obtaining an animal including the same genetic information as another animal cell including donor nucleus by carrying out steps of: removing a nucleus from the animal oocyte and introducing the donor nucleus from the other animal cell into the animal oocyte; performing reprogramming of the oocyte which is introduced the donor nucleus; performing differentiation of the reprogrammed oocyte; and transplanting the differentiated oocyte into a surrogate mother.

Somatic Cell Nuclear Transfer (SCNT)

"Somatic cell nuclear transfer (SCNT)" refers to nuclear transfer carried out for a case in which the cells including a donor nucleus are the somatic cells. The 'Somatic cell nuclear transfer (SCNT)' includes a technology for obtaining an animal with the same genetic information as a somatic cells by performing the aforementioned steps, when animal cells including the donor nucleus are the somatic cells.

A transformed animal can be produced by delivering materials for genetic engineering into cells including a donor nucleus. For example, a transformed animal can be produced by SCNT, following microinjection the materials for genetic engineering into the somatic cell.

Culture Medium or Culture Medium Composition

"Culture medium" or "culture medium composition" refers to a mixture for growth and proliferation of cells or the like in in-vitro or ex-vivo. The mixture includes elements that are essentially required for the growth and proliferation of cells or the like, e.g., the elements include sugars, amino acids, various nutrients, serum, growth factors, minerals, or the like.

Treatment

"Treatment" refers to a measure for obtaining beneficial or desirable clinical results. For the purpose of the present specification, the beneficial or desirable clinical results include, although not limited thereto, palliation of the symptoms, reduction in the disease range, stabilization of the disease state (i.e., no aggravation), delay or slowing down the progress of disease, improvement of the disease state, temporary palliation and reduction (either partially or entirely) of the disease state, and whether the disease is detectable or non-detectable. "Treatment" refers to both the therapeutic treatment and preventing or prophylactic methods. Those treatments include not only a treatment for a disorder which can be prevented but also a treatment required for a pre-existing disorder. "Palliating" a disease refers to the range of disease state and/or undesirable clinical signs are diminished; and/or time course of the progress of disease is either delayed or extended, compared to the case in which treatment is not performed.

About

"About" refers to a quantity, level, value, number, frequency, percentage, dimension, size, amount, weight or length that varies by as much as 30%, 25%, 20%, 15%, 10%, 9%, 8%, 7%, 6%, 5%, 4%, 3%, 2% or 1% to a reference quantity, level, value, number, frequency, percentage, dimension, size, amount, weight or length.

Background Knowledge—Hemophilia and F9 Factor

Hemophilia

"Hemophilia B", or Christmas disease, is a hereditary X-linked recessive hemorrhagic disorder caused by a defective F9 factor (ninth clotting factor, FIX). Hemophilia is a disease that is related to deficiency of which the amount or activity of the F9 factor.

Herein, symptoms of hemophilia, i.e., bleeding form, include: an injury or bleeding of central nervous system (including lumbar puncture, epidural anesthesia, or the like); bleeding in space behind peritoneum; tooth extraction involving anesthesia; severe gastrointestinal tract bleeding; bleeding in upper airway and respiratory tract; bleeding in joint cavity and muscle bleeding; superficial hematoma; bleeding in oral cavity; bleeding under tooth; nose bleeding; mild hematuria; and severe menstrual bleeding. The bleeding in joint cavity refers to bleeding occurring in a knee, elbow, ankle, shoulder, hip (hip joint), wrist, or the like.

"Spontaneous bleeding" is also referred to as spontaneous hemorrhage or spontaneous internal bleeding, and it refers to bleeding which suddenly occurs in everyday life without trauma, any specific factors, or previous signs. Spontaneous bleeding in joint and/or muscle is often shown in hemophilia B. Spontaneous internal bleeding may occur in one or more region of a joint, muscle, gastrointestinal duct, brain, kidney, nose, and eye. These spontaneous bleeding induces complications, and examples of representative symptoms shown in hemophilia include joint deformity or joint inflammation which are caused by repeated bleeding in joint. Accordingly, it is also important to develop a therapeutic agent for preventing or treating spontaneous hemorrhage as a hemophilia B therapeutic agent.

"External bleeding" refers to visible bleeding on exterior body parts, namely, bleeding caused by external wound such as incised wound, tooth extract, symptoms of continuous bleeding from surgical site or the like.

F9 Factor

"Factor 9 (hereinbelow, referred to as 'F9')" is one of the blood coagulation factors, and it is an essential protein for forming blood clot. Herein, F9 factor refers to the molecule of ninth factor in certain form with representative property of the ninth blood coagulation factor. F9 factor is a mono-saccharide-chain glycoprotein in blood plasma playing an essential role in intrinsic blood coagulation pathway, in which the F9a factor (FIXa), i.e., active form of F9 factor, interacts with F8a factor, phospholipids, and calcium ions to form a "tenase" complex, which converts F10 factor to F10a factor. F9 factor consists of Gla domain, two EGF domains (EGF-1 and EGF-2), AP region, and serine protease domain.

Unlike the wild type F9 factor, "mutant F9 factor" can be a F9 factor with reduced or lost protein function due to an occurrence of natural, or artificial modification (i.e., artificially modified or artificially engineered).

"Wild type" refers to a gene most commonly observed in nature or any allele gene designated to be normal. It can be in form of a steady-state gene exhibiting no specific disorder, for example.

Expression "artificially modified or artificially engineered" refers to a state to which modification is artificially applied instead of the presence itself occurring in nature. For example, a state to which modification is artificially applied can be a modification for causing artificially a mutation in a wild type gene. Hereinbelow, the expression "artificially modified F9 gene" can be interchangeably used with the expression "artificial F9 gene".

The F9 factor can be F9 gene expressed by NCBI Accession No. NM_031540, for example, but it is not limited thereto.

Background Knowledge—Methods for Artificial Engineering or Modification of Gene

Methods for Artificial Engineering or Modification of Gene—Introduction

Methods for artificial engineering of gene includes a technology using engineered nuclease, a technology using antisense RNA, a technology using mutant gene or protein, or the like.

"Engineered nuclease (programmable nuclease)" includes all types of nucleases which can recognize and cleave a specific site on a target gene. Engineered nuclease may recognize a specific nucleotide sequence in genome of a prokaryotic cell and/or an animal/plant cell including human cell (e.g., eukaryotic cell) to cause double strand break (DSB). DSB may yield, according to break of DNA double strand, a blunt end or a cohesive end. In cells, DSB can be efficiently repaired by homologous recombination or non-homologous end-joining (NHEJ) mechanism. Herein, the engineered nuclease is an enzyme which can cause a substitution, an insertion, or a deletion of one or more nucleotides.

For example, an engineered nuclease causing artificial modification within a gene can be TALEN (transcription activator-like effector nuclease) which is fused a TAL effector (transcription activator-like effector) domain originating from plant pathogenic gene, which is the domain recognizing a specific target sequence on genome, and a cleavage domain; zinc-finger nuclease; meganuclease; CRISPR-enzyme protein; Cpf1 protein; or the like.

The engineered nuclease may form complementary bonds with whole or part of the nucleotide sequence of a genome.

The engineered nuclease may cause artificial modification of a gene based on complete gene removal, deletion or substitution of part of the nucleotide sequence in F9 gene, or insertion of an exogenous nucleotide.

The engineered nuclease may cause artificial modification of F9 gene according to forming complementary bonds to a partial nucleotide sequence of an exon region, an intron region, a regulatory region, a splicing site, a 5' terminus or an adjacent region thereof, or a 3' terminus or an adjacent region thereof in the gene.

Subject for Artificial Engineering

Subject for the "artificial engineering" can be a target nucleic acid, a target gene, a target chromosome, or a target protein.

For example, the engineered nuclease can engineer or modify a target sequence in a gene, thereby regulating the amount, activity, or function of a protein to be expressed; or causing the expression of a modified protein.

For example, the engineered nuclease can engineer or modify a target sequence in a gene, thereby suppressing, inhibiting, reducing, promoting, or enhancing the protein expression level.

For example, the engineered nuclease can engineer or modify a target sequence in a gene, thereby suppressing, inhibiting, reducing, promoting, or enhancing the activity of a protein expression.

For example, the engineered nuclease can engineer or modify a target sequence in a gene, thereby removing, reducing, adding, or enhancing the function of a protein.

One or more of the genetic engineering technologies can be applied to gene transcription and translation stages.

For example, one or more of the genetic engineering technologies can engineer or modify a target sequence which regulates the transcription, thereby promoting or inhibiting transcription.

For example, one or more of the genetic engineering technologies can engineer or modify a target sequence which regulates the protein translation, thereby regulating protein expression.

CRISPR-Enzyme System (Guide Nucleic Acid and Editor Protein)

As a method for artificial gene engineering, CRISPR-enzyme system can be used.

CRISPR-enzyme system consists of a guide nucleic acid and/or an editor protein.

The term "guide nucleic acid" refers to a nucleotide sequence capable of recognizing a target nucleic acid, a target gene, or a target chromosome and interacting with an editor protein. Herein, the guide nucleic acid may form a complementary bond with a partial nucleotide in target nucleic acid, target gene, or target chromosome.

The guide nucleic acid can be in the form of a target DNA-specific guide RNA, a DNA encoding the guide RNA, or DNA/RNA mixture.

The guide nucleic acid can be a guide RNA.

"Guide RNA" can be in vitro transcribed, and can be, in particular, transcribed from a double stranded oligonucleotide or a plasmid template, but it is not limited thereto.

Designs and configurations of the guide RNA are well known to a person skilled in the art. They are also explained in detail in Korean Patent Application Publication No.

10-2018-0018457 and the disclosure of the publication is incorporated herein by reference in its entirely.

"Editor protein" refers to a peptide, a polypeptide, or a protein which can directly bind to a nucleic acid or interacts with a nucleic acid without direct binding. In concept, the editor protein is also referred to as "artificially engineered nuclease" or RGEN (RNA-Guided Endonuclease).

In one specific embodiment, the editor protein can be a CRISPR enzyme.

"CRISPR enzyme" is a main constitutional protein element of CRISPR-enzyme system, and it refers to a nuclease which can, by forming a mixture or a complex with guide RNA, recognize a target sequence and cleave DNA.

CRISPR enzyme is well known to a person skilled in the art, and references Korean Patent Application Publication No. 10-2018-0018457.

In the present specification, the CRISPR enzyme can be used as a concept including all variants capable of functioning as an activated endonuclease or nickase in cooperation with a guide RNA in addition to wild type proteins. In case of activated endonuclease or nickase, the cleavage of a target DNA can be induced, and can lead to genome editing. In addition, in case of an inactivated variant, the transcription regulation or isolation of a desired DNA can be achieved by using it.

The isolated Cas protein can be also in form of easy to be introduced into a cell. For example, Cas protein can be linked to a cell penetrating peptide or a protein transduction domain. The protein transduction domain can be polyarginine or TAT protein originating from HIV, but it is not limited thereto. As for the cell penetrating peptide or protein transduction domain, various types other than those described above are well known in the art so that, without being limited to the above examples, various examples can be applied to the present specification by a skilled person.

Zinc-Finger Nuclease

"Zinc-finger DNA binding protein" (or binding domain) indicates a protein which binds to a DNA in sequence-specific manner via at least one zinc-finger, which is an amino acid sequence region in binding domain with structure stabilized by zinc ion coordination, or a domain in a larger protein. The expression "zinc-finger DNA binding protein" is mainly abbreviated as zinc-finger protein or ZFP.

The zinc-finger nuclease (ZFN) comprises a zinc finger protein engineered to bind to a target gene and to a target site in a cleavage domain or a cleavage half-domain. The ZFN can be an artificial restriction enzyme comprising a zinc-finger binding domain and a DNA cleavage domain. Herein, the zinc finger binding domain can be a domain which has been engineered to bind to a selected sequence. For example, Beerli et al. (2002) Nature Biotechnol. 20:135-141; Pabo et al. (2001) Ann. Rev. Biochem. 70:313-340; Isalan et al, (2001) Nature Biotechnol. 19:656-660; Segal et al. (2001) Curr. Opin. Biotechnol. 12:632-637; Choo et al. (2000) Curr. Opin. Struct. Biol. 10:411-416 can be incorporated herein by reference. Compared to naturally occurring zinc finger proteins, the engineered zinc finger binding domain may have novel binding specificities. The method of engineering includes rational design and selection of various types, but it is not limited thereto. The rational design includes the use of database including, for example, triple (or quadruple) nucleotide sequences and individual zinc finger amino acid sequences, wherein each triple or quadruple nucleotide sequence is combined with one or more sequences of a zinc finger that binds to a particular triple or quadruple sequence.

With regard to the ZFN, selection of target gene and target sequence sequences and design and construction of the fusion protein or a polynucleotide encoding the fusion protein are well known to those skilled in the art, and they are described in detail in U.S. Patent Application Publication Nos. 2005/0064474 and 2006/0188987, the disclosures of which are incorporated herein by reference by their entirety. Further, as disclosed in those and other references, zinc finger domains and/or multi-finger zinc finger proteins can be linked by a linker comprising any appropriate linker sequence, for example, a linker with length of 5 or more amino acids. Examples of linker sequences with length of 6 or more amino acids are disclosed in U.S. Pat. Nos. 6,479, 626, 6,903,185, and 7,153,949. The proteins described herein may comprise any combination of appropriate linkers between each zinc finger of the protein.

A nuclease such as ZFN comprises a cleavage domain and/or a cleavage half-domain, which are/is the active part of nuclease.

For example, the cleavage domain can be a cleavage domain derived from a nuclease which is different from zinc-finger DNA binding domain, i.e., heterologous cleavage domain.

In another example, the cleavage half-domain can be a fusion protein derived from any nuclease which requires dimerization for the cleavage activity, or a part thereof. When the fusion protein comprises a cleavage half-domain, generally two fusion proteins can be required for cleavage. Alternatively, a single protein comprising two cleavage half-domains can be utilized.

The two cleavage half-domains can be derived from the same endonuclease (or functional fragments thereof), or each can be derived from a different endonuclease (or functional fragments thereof). Further, the target site of the two fusion proteins is preferably arranged such that the cleavage half domain can form functional cleavage domains by, for example, dimerization, with the cleavage half domains being arranged to each other in spatial orientation by the binding of the two fusion proteins and their respective target sites.

TALEN System

"TALEN" indicates a nuclease capable of recognizing and cleaving a target region in DNA. TALEN is a fusion protein comprising a TALE domain and a nucleotide cleavage domain. In the present specification, the terms "TAL effector nuclease" and "TALEN" are interchangeable. The TAL effector is known to be a protein secreted by the type secretion system of *Xanthomonas* bacteria, when a variety of plant species are infected by the bacteria. The protein may bind to a promoter sequence in a host plant to activate the expression of a plant gene that aids in bacterial infection. The protein recognizes plant DNA sequences through a central repeating domain which is composed of a variable number of amino acid repeats up to 34.

"TALE domain" or "TALE" is a polypeptide comprising at least one TALE repeat domain/unit. The repeat domain is related to binding between TALE and homologous target DNA sequence thereof. Single "repeat unit" (also referred to as "repeat part") typically has length of 33 to 35 amino acids, and it shows at least partial sequence homology with other TALE repeat sequence within naturally occurring TALE protein. The TALE domain is a protein domain which binds, via one or more TALE-repeat modules, to a nucleotide in sequence-specific manner.

The TALE DNA binding domain comprises at least one TALE-repeat module, more particularly, 1 to 30 TALE-repeat module modules, but it is not limited thereto. As described herein, "TALE DNA binding domain", "TALE domain", and "TALE effector domain" can be interchangeably used.

The TALE DNA binding domain may comprise half of a TALE-repeat module. With regard to TALE, disclosures of International Publication WO/2012/093833 and U.S. Patent Laid-Open No. 2013-0217131 are incorporated herein by reference in their entirety.

Meganuclease

The meganuclease can be a naturally-occurring meganuclease, although it is not limited thereto. It recognizes cleavage sites of 15 to 40 base pairs, which are commonly grouped into four families: LAGLIDADG family, GIY-YIG family, His-Cyst box family, and HNH family. Examples of the meganuclease include I-SceI, I-CeuI, PI-PspI, PI-SceI, I-SceIV, I-CsmI, I-PanI, I-SceII, I-PpoI, I-SceIII, I-CreI, I-TevI, I-TevII, and I-TevIII.

The artificially engineered meganuclease is a meganuclease which has been genetically engineered to have novel binding specificity. Naturally occurring or artificially engineered DNA binding domain derived from meganuclease can be linked to a cleavage domain derived from a heterologous nuclease (e.g., FokI) to cause one or more gene modifications in a gene, thereby yielding knock-down or knock-out.

Use of RNAi

Genetic engineering technology using an "antisense RNA" allows small RNA (sRNAs) to interfere, reduce, or, depending on the case, disrupt mRNA based on RNA interference (RNA silencing) so that the information for protein synthesis is not to be delivered. By using an antisense RNA, expression of genetic information can be controlled.

For example, gene expression can be weakened or disrupted by using the antisense RNA technology.

In an embodiment, the genetic engineering technology using antisense RNA can be one or more of small interfering RNA (hereinbelow, referred to as 'siRNA'), short hairpin RNA (hereinbelow, referred to as 'shRNA'), and microRNA (hereinbelow, referred to as 'miRNA').

The antisense RNA may form a complementary bond with a partial nucleotide sequence of a gene, and it may also regulate gene expression.

For example, it may form a complementary bond with a partial nucleic acid sequence of an exon region, an intron region, a regulatory region, a splicing site, a 5' terminus or an adjacent region thereof, or a 3' terminus or an adjacent region thereof in a gene.

Others

For engineering the factors to be expressed by the aforementioned gene other than direct genetic engineering, a dominant negative mutant, ribozyme, an intracellular antibody, a peptide or a small molecule can be used.

For example, by allowing expression of the dominant negative mutant in a cell, factors having no normal function can be expressed in the cell.

In another example, by using a peptide or a small molecule, or the like, it is possible to induce a target factor not to function normally in a cell.

Background Knowledge—Delivery of Materials for Genetic Engineering

Delivery of Materials for Genetic Engineering—Introduction

Hereinbelow, a method for the aforementioned artificial genetic engineering, i.e., method for delivery of materials for genetic engineering to a subject (e.g., cells or the like) of genetic engineering, is explained in detail.

Delivery of Materials for Genetic Engineering; 1—Vector

Materials for genetic engineering can be delivered by using a naked nucleic acid vector, a non-viral vector, or a viral vector.

The vector can be a viral vector or a non-viral vector (e.g., plasmid).

The term "vector" can deliver a gene sequence to a cell. Typically, "vector construct", "expression vector", and "gene delivery vector" refer to any nucleic acid structure capable of indicating the expression of a gene of interest and delivering a gene sequence to a target cell.

As a method for artificial gene modification by introducing into a cell, the vector can use a known expression vector such as plasmid vector, cosmid vector, bacteriophage vector, or the like, and the vector can be easily produced by a person skilled in the art according to any known method using DNA recombination technology.

"Gene delivery vector" refers to any nucleic acid structure capable of indicating the expression of a gene of interest and delivering a gene sequence to a target cell Thus, the term includes a cloning vector, an expression vehicle, and an integration of vector.

The vector can be a recombinant expression vector. For example, it can be a vector comprising materials for genetic engineering.

The recombinant expression vector for artificial modification of a gene may include a promoter. The promoter can utilize a promoter in the art.

"Promoter" refers to regulatory sequences which are nucleotide sequence regions for controlling initiation and speed of transcription. These promoters can include gene elements enabling the initiation of specific transcription of a nucleotide sequence by binding transcription factors which are RNA polymerase, other regulatory proteins, and the likes. Terms like "effectively aligned", "effectively bound", "under regulation" and "under transcription regulation" refer to the promoter is aligned at correct activation position and/or in correct orientation with regard to the nucleotide sequence which regulates the initiation and expression of the sequence.

For example, the promoter can be either an endogenous promoter in a target region or an exogenous promoter. The promoter can be a promoter which is recognized by RNA polymerase II or RNA polymerase III. The promoter can be a constitutive promoter, an inducible promoter, a subject-specific promoter, a viral promoter, or a non-viral promoter.

As for the promoter, it is possible to use a suitable promoter (i.e., guide RNA, CRISPR enzyme). For example, a promoter useful for the guide RNA can be a H1, EF-1a, tRNA, or U6 promoter. For example, a promoter useful for the editor protein can be a CMV, EF-1a, EFS, MSCV, PGK, or CAG promoter.

The recombinant expression vector for artificial modification of a gene may comprise a reporter gene, and the reporter gene may comprise a reporter system.

Furthermore, the recombinant expression vector for artificial modification of a gene may comprise a selection marker. Examples of the selection marker include an antibiotic resistance resistant gene such as kanamycin resistant gene or neomycin resistant gene, and a fluorescent protein such as green fluorescent protein and red fluorescent protein, but it is not limited thereto.

Furthermore, the recombinant expression vector for artificial modification of a gene may comprise a tag sequence for isolation, purification, or identification of a protein.

Examples of the tag sequence include GFP, GST (Glutathione S-transferase)-tag, HA, His-tag, Myc-tag, and T7-tag, but the tag sequence of the present invention is not limited by those examples.

Furthermore, the recombinant expression vector for artificial modification of a gene may comprise, other than those described above, a replication origin, an enhancer, any essential ribosome binding site, a Kozak consensus sequence, a polyadenylation site, a splice donor, and a receptor site, a transcription termination site, 5' flanking non-transcription sequence, an intein, and/or a 2A sequence.

Delivery of Materials for Genetic Engineering; 2—Viral Delivery

The genetic engineering technology can be delivered to a cell by using virus.

The viral delivery can use an RNA-based viral vector. The RNA-based viral vector can include an oncoretroviral vector, a lentiviral vector, and a human foamy viral vector, but it is not limited thereto.

The viral delivery can use a DNA-based viral vector. The DNA-based viral vector can include an adenovirus, an adeno-associated virus, an Epstein-Barr virus, a herpes simplex virus, and a poxvirus, but it is not limited thereto.

The viral delivery has an advantage in which the delivery efficiency of large-size gene is good.

The materials for genetic engineering can be delivered to a subject by using one or more vectors.

For example, when the materials for genetic engineering are a guide RNA and an editor protein, the editor protein and the guide RNA can be delivered after being encoded in vectors that are different from each other.

When the materials for genetic engineering are delivered to a genome by using 2 or more vectors, the same type or different type vector can be used.

For example, the guide nucleic acid can be delivered by using a plasmid, while the editor protein can be delivered by using a viral vector.

Delivery of Materials for Genetic Engineering; 3—Non-Viral Delivery

The materials for genetic engineering can be delivered into a cell by using non-virus.

The non-viral delivery can use a naked nucleic acid vector. The naked nucleic acid vector can include a circular nucleic acid vector a linear nucleic acid vector, but it is not limited thereto.

The non-viral delivery can use a non-viral vector. The non-viral vector can comprise an artificial chromosome, a liposome, a polymer, a lipid-polymer hybrid, an inorganic nanoparticle, and an organic nanoparticle, but it is not limited thereto.

Examples of the non-viral delivery include microinjection, gene gun, electroporation, sonoporation, photoporation, magnetofection, hydroporation, but it is not limited thereto.

'Microinjection' refers to the injection of a material to an organ, a tissue, a cell, or a small organelle in cell of a living organism. Examples of the material include a chemical compound, a polynucleotide, and a polypeptide.

Examples of the microinjection include gamete microinjection, embryo microinjection, and somatic cell microinjection.

The embryo microinjection refers to the microinjection of a material including polynucleotide into an embryo, and it includes a technology of obtaining a transformed animal by microinjection of a material including polynucleotide to an embryo followed by differentiation step or the like.

The somatic cell microinjection refers to the microinjection of a material including polynucleotide into a somatic cell. According to a nuclear transfer following the microinjection to a somatic cell, a transformed animal can be obtained.

For example, when the materials for genetic engineering are a guide RNA and an editor protein, the guide RNA-editor protein complex can be delivered to an inside of a cell by microinjection. Namely, the delivery can be made in form of a ribonucleoprotein (RNP). The guide RNA-editor protein complex refers to a complex formed by an interaction between the guide RNA and CRISPR enzyme.

Limitations of Conventional Technologies

Conventionally, as a hemophilia B animal model, mice have been mainly used as animals for disease models, which they have short life cycle and short reproduction cycle, can be easily kept, and are relatively inexpensive in terms of the cost. On the other hand, the animal model using mice is not useful for providing a medical opinion regarding some symptoms caused by hemophilia, and thus studies are continued for developing an animal model which has similar disease-induced mechanisms and symptoms of hemophilia patients.

In particular, as a conventional animal model for hemophilia B, mice do not exhibit spontaneous bleeding in tissues of joints, muscles or the like, which is one of the representative symptoms of hemophilia, and thus they are inappropriate to be used as an animal disease model for developing or producing the pharmaceuticals for hemophilia B. In addition, other mammals like dog also have a limitation in terms of breeding and cost, when compared to rodents.

Accordingly, there is an increasing demand for producing an animal model which is more suitable in terms of the genetic similarity with humans; breeding; cost; and use as an animal disease model. At the present moment, a hemophilia B animal model using rat was not developed.

Hemophilia B Rat Model

Hemophilia B Rat Model—Introduction

According to the present specification, a hemophilia B rat is provided as a hemophilia B animal model. The hemophilia B rat is characterized by 1) having artificially modified F9 gene, 2) including artificially modified F9 factor due to 1), and 3) exhibiting a bleeding symptom (e.g., continuous bleeding and/or spontaneous bleeding). Accordingly, the hemophilia B rat has an advantage that it can be a suitable animal model for hemophilia B.

Characteristic of Hemophilia B Rat Model; 1—Including Artificially Modified F9 Gene One embodiment disclosed in the present application relates to a hemophilia B rat which has artificial modification occurred in the genome. The hemophilia B rat, which has artificial modification occurred in the genome, includes F9 gene of which a part or all gene is engineered and/or modified.

For example, the hemophilia B rat model may have a downregulation or loss of the expression or function of F9 factor. Specifically, F9 gene can be either knocked down or knocked out, but it is not limited thereto.

Hereinbelow, "rat including an artificially modified F9 factor or a nucleic acid encoding the artificially modified F9 factor" and "artificially modified rat" can be used interchangeably. Hereinbelow, the "artificially modified F9 gene" is described in detail. Artificially modified F9 gene 1-Modified form of F9 gene In one embodiment, the artificially modified F9 gene includes artificial modification on an exon, an intron, a regulatory region, a 5' terminus or an adjacent region thereof, 3' terminus or an adjacent region thereof, a splicing site, or the like.

For example, the artificially modified F9 gene may include one or more artificial modifications in one region within the first exon region or the second exon region.

In another example, the artificially modified F9 gene may include one or more artificial modifications in one region within a regulatory region (enhancer, promoter, 3 'UTR and/or non-coding sequence of polyadenylation signal).

In another example, the artificially modified F9 gene may include one or more artificial modifications in one region within a 5' terminus or an adjacent region thereof, or a 3' terminus or an adjacent region thereof In still another example, the artificially modified F9 gene may include one or more artificial modifications in one region within a splicing site.

The one region ('target site') of F9 gene to be modified can be a continuous nucleotide sequence site with about 1 bp, about 2 bp, about 3 bp, about 4 bp, about 5 bp, about 6 bp, about 7 bp, about 8 bp, about 9 bp, about 10 bp, about 11 bp, about 12 bp, about 13 bp, about 14 bp, about 15 bp, about 16 bp, about 17 bp, about 18 bp, about 19 bp, about 20 bp, about 21 bp, about 22 bp, about 23 bp, about 24 bp, about 25 bp, about 26 bp, about 27 bp, about 28 bp, about 29 bp, about 30 bp, about 40 bp, or about 50 bp of the aforementioned gene. The target site in F9 gene can be a continuous nucleotide sequence in the aforementioned gene, having a length between two numerical ranges selected from the previous sentence. The target site in F9 gene can be a continuous nucleotide sequence in the aforementioned gene site, having a length longer than or equal to one numerical value selected from the previous sentence.

Modification of the F9 gene nucleotide sequence includes an addition, a deletion, or a substitution of one or more nucleotides in the genome, but it is not limited thereto.

It may include insertion of one or more nucleotides in nucleotide sequence of F9 gene, deletion of one or more nucleotides in nucleotide sequence of F9 gene, substitution of one or more nucleotides in nucleotide sequence of F9 gene, knock-out of a nucleotide sequence or a part thereof in F9 gene, knock-down of a nucleotide sequence or a part thereof in F9 gene, or the like.

For example, the F9 gene modification can be induced by one or more of the followings:

1) deletion of a whole or partial sequence of F9 gene, for example, deletion of a 1 bp or longer nucleotides of F9 gene, e.g., the nucleotides are 1 to 50, 1 to 30, 1 to 27, 1 to 25, 1 to 23, 1 to 20, 1 to 15, 1 to 10, 1 to 5, 1 to 3 nucleotides, or 1 nucleotide of F9 gene;

2) substitution of a 1 bp or longer nucleotides of F9 gene, e.g., the nucleotides are 1 to 30, 1 to 27, 1 to 25, 1 to 23, 1 to 20, 1 to 15, 1 to 10, 1 to 5, 1 to 3 nucleotides or 1 nucleotide of F9 gene; and 3) insertion of one or more nucleotides from a foreign gene into an arbitrary site of F9 gene, e.g., the nucleotides are 1 to 30, 1 to 27, 1 to 25, 1 to 23, 1 to 20, 1 to 15, 1 to 10, 1 to 5, 1 to 3 nucleotides or 1 nucleotide (nucleotides are each independently selected from A, T, C and G).

As a result of the modification of one or more nucleotide sequences in exon or intron, reduction or loss of the transcription amount of F9 gene, reduction or loss of the expression of F9 factor, or inhibition and inactivation of the function and/or activity of F9 factor can be caused.

As a result of the modification of one or more nucleotide sequences in regulatory region, splicing site, 5' terminus or an adjacent region thereof, or 3' terminus, reduction or loss of the expression of F9 factor, or inhibition and inactivation of the function and/or activity of F9 factor can be caused.

In another example, the hemophilia B rat having an artificial modification occurred in the genome may have completely removed F9 gene. Namely, the hemophilia B rat can include modification showing removal of the entire F9 gene by artificial engineering or modification.

In one embodiment, a partial nucleotide sequence of both terminals of the F9 gene and/or adjacent regions of both terminals can be cleaved and/or removed, either simultaneously or sequentially. In another embodiment, the F9 gene can be completely removed.

Artificially Modified F9 Gene 2—Artificially Modified F9 Factor

The artificial modification in genome can cause a mutation of F9 factor. Namely, the hemophilia B rat may include an artificially modified F9 factor.

In one specific example, the artificially modified F9 factor can be a F9 factor of which one or more amino acid sequences are altered.

One or more amino acids in F9 factor can be altered to an amino acid with similar property.

For example, hydrophobic amino acids in the F9 polypeptide can be altered to another hydrophobic amino acids. Hydrophobic amino acid is any one of glycine, alanine, valine, isoleucine, leucine, methionine, phenylalanine, tyrosine, arginine, and histidine.

In another example, acidic amino acids in the F9 polypeptide can be altered to another acidic amino acids. Acidic amino acid is any one of glutamic acid and aspartic acid.

In another example, polar amino acids in the F9 polypeptide can be altered to another polar amino acids. Polar amino acid is any one of serine, threonine, asparagine, and glutamine.

One or more amino acids in F9 factor can be altered to an amino acid with different property.

For example, hydrophobic amino acids in the F9 polypeptide can be altered to any one amino acid from serine, threonine, asparagine, and glutamine that are polar amino acids.

In another example, hydrophobic amino acids in the F9 polypeptide can be altered to any one amino acid from glutamic acid and aspartic acid that are acidic amino acids.

In another example, hydrophobic amino acids in the F9 polypeptide can be altered to any one amino acid from arginine and histidine that are basic amino acids.

In another example, polar amino acids in the F9 polypeptide can be altered to any one amino acid from glycine, alanine, valine, isoleucine, leucine, methionine, phenylalanine, tyrosine, and tryptophan that are hydrophobic amino acids.

In another example, acidic amino acids in the F9 polypeptide can be altered to any one amino acid from arginine and histidine that are basic amino acids.

As still another example, basic amino acids in the F9 polypeptide can be altered to any one amino acid from glutamic acid and aspartic acid that are acidic amino acids.

In summary, the expression level of protein can be regulated by alteration and/or substitution of the amino acid described above.

Alternatively, the structure and function of protein can be affected by alteration and/or substitution of the amino acid described above.

Thus, in one embodiment, by the artificial modification of the F9 factor, the hemophilia B rat may include: the F9 factor which is not expressed at all; the F9 factor of which expression is inhibited; and/or the F9 factor of which expression level is reduced. In another embodiment, the hemophilia B rat may include F9 factor with hypofunction or lost function.

Characteristic of Hemophilia B Rat Model; 2—Occurrence of Bleeding Symptom

The artificially modified rat may exhibit a bleeding symptom (continuous bleeding, spontaneous bleeding). In one embodiment, the artificially modified rat may exhibit spontaneous bleeding and/or external bleeding. In one embodiment, the artificially modified rat includes spontaneous bleeding in tissues.

In another embodiment, the artificially modified rat may include inflammation caused by the spontaneous bleeding in tissues; and/or swelling caused by the spontaneous bleeding in tissues, in which the tissues can be joint, muscle, or eye.

In particular, the artificially modified rat may exhibit spontaneous bleeding that is not shown from mice.

Advantage of Hemophilia B Rat Model; 1—Advantage of Rat Itself

Rat has high genetic similarity with humans, and it also has an advantage of a mouse as an animal model. For example, in terms of the nutrition or metabolism and physiology, rat has higher similarity with humans compared to the animals of other types. Furthermore, the weight ratio of muscles, organs, or the like is similar to that of humans, sexual cycle can be more conveniently and regularly determined due to its endocrinal or reproductive system, and the menstrual cycle is also highly similar to the cycle of humans. Furthermore, compared to a mouse, a rat has almost the same reproductive ability with shorter growth period, and, due to a larger size, it is more appropriate for surgical operation. Still furthermore, a greater amount of sample can be collected from the rat, and, since the disease symptoms shown in mammals are also closer to humans compared to mouse, it is indeed a reliable animal disease model.

Advantage of Hemophilia B Rat Model; 2—Advantage as Hemophilia B Model

Various bleeding symptoms (e.g., spontaneous bleeding symptom) is one of the representative symptoms of hemophilia B. When spontaneous bleeding occurs in knee joint or the like, in particular, there are problems of having arthritis or the like so that a demand for development of a therapeutic agent is highly increasing. (During the process of developing a therapeutic agent, it is essential to use an animal model suitable for the corresponding disease. However, the mice model as a hemophilia B which has been generally used before exhibits no such various bleeding symptoms, and thus it cannot be an effective animal model. In addition, although mammalian animals like dog have an advantage that they allow production of an animal model closer to humans, they have problems that breeding is not easy and cost for test is very high. Thus, they cannot be used as an animal model. On the other hand, the hemophilia B rat model provided in the present specification has advantages that 1) due to a characteristic of exhibiting various bleeding symptoms as representative symptom of hemophilia B (e.g., spontaneous bleeding), it is suitable as an animal model for hemophilia B, and 2) due to the aforementioned advantages of a rat itself like easy breeding, low cost, or the like, it can be used as an efficient animal model. Therefore, the hemophilia B rat model is an animal model which overcomes the limitation of existing mouse model, and it is an animal model which is suitable in terms of the development and production of a therapeutic agent and also the evaluation of toxicity and stability.

Type of Rat—Example

Rat belongs to the genus *Rattus* of family Muridae, and it is distinguished from a mouse belonging to the genus Mus. Examples of the rat include Wistar rat, Long-Evans rat, Sprague Dawley rat, Zucker rat, Biobreeding rat, Brattleboro rat, and Hairless rat.

As for the rat disclosed in the present specification, any kind of known rats which can be suitably selected and used by a person skilled in the art can be used.

Cell Including Artificially Modified F9 Gene

Cell Including Artificially Modified F9 Gene—Introduction

One embodiment disclosed in the present application relates to a cell including an artificially modified F9 factor and/or a gene encoding the artificially modified F9 factor. The cell can be used for producing the hemophilia B rat model. The cell can be used independently from the hemophilia B rat model according to the purpose.

Subject Cell—Example

The cell can be a transformed stem cell, a transformed embryonic cell, or a transformed somatic cell.

In any specific example, the cell can be a cumulus cell, an epidermal cell, a fibroblast cell, a nerve cell, a keratinocyte cell, a hematopoietic cell, a melanin cell, a chondrocyte cell, a macrophage, a monocyte, a muscle cell, a B lymphocyte, a T lymphocyte, an embryonic stem cell, an embryonic germ cell, a fetus-derived cell, a placenta cell, an embryonic cell, or the like. Furthermore, an adult stem cell derived from various tissue-of-origin can be used. For example, a stem cell derived from tissues such as adipose tissue, uterus, bone marrow, muscle, placenta, cord blood, or skin (epithelium) can be used. Generally, a non-human host embryo can be an embryo at 2-cell stage, 4-cell stage, 4-cell stage, 8-cell stage, 16-cell stage, 32-cell stage, or 64-cell stage, or an embryo including morula or blastocyst.

In another specific embodiment, the cell can be a hepatocyte,

The embryonic cell, somatic cell, or stem cell can be obtained by a method of preparing a sample for a surgical specimen or a biopsy sample using conventional methods well known in the art.

Transformed Cell

'Transformed cell' can be a somatic cell or an embryonic cell including a transformed part in genome in the cell. Hereinbelow, the transformed somatic cell or embryonic cell can be interchangeably used with the term 'transformed cell.' The transformed cell includes a second cell obtained by cell division from a first cell division from a first cell including the transformed part. In this case, the second cell obtained by cell division includes a part with the same nucleotide sequence as the transformed part of the first cell.

The transformed cell includes artificially modified F9 gene. The artificially modified F9 gene has the same meaning as defined above.

In one example, the transformed cell may include a gene in which an insertion, a deletion, or a substitution of nucleotides has occurred in one or more regions in F9 gene.

In another example, the transformed cell can be a cell having the F9 gene knocked down and/or knocked out.

The transformed cell can be a cell in which F9 factor is not present at all or in which the expression level of F9 factor is reduced.

The transformed cell can be a cell in which F9 factor has hypofunction or lost function.

The transformed cell can be a cell deficient of F9 factor.

Including Materials for Genetic Engineering

The transformed cell may include a material for genetic engineering targeting F9 factor, i.e., engineered nuclease, antisense RNA, dominant negative mutant F9, ribozyme, or the like.

For example, the transformed cell includes CRISPR-Cas system, ZFN, TALEN or meganuclease, or a nucleic acid encoding them Alternatively, the transformed cell includes small interfering RNA (siRNA), short hairpin RNA (shRNA), or microRNA, or a nucleic acid encoding them, for example.

Alternatively, the transformed cell includes dominant negative mutant F9 targeting F9 factor or a ribozyme against nucleic acid encoding F9 factor, or a nucleic acid encoding them.

The material for genetic engineering is included in various forms in a cell. For example, it can be in form of a vector which includes a nucleic acid encoding the material for genetic engineering.

Possibility of Forming Cell Colony

The transformed cell can form a cell colony. The cell colony can be a single cell cultured from single cells.

Herein, the cell colony can be a colony which is formed only of the cells having all F9 factor knocked down or knocked out.

Alternatively, the cell colony can be a chimeric cell colony including normal F9 factor that is not knocked down or knocked out.

Composition for Engineering F9 Gene to Produce Hemophilia B Rat Model

Composition for Engineering F9 Gene to Produce Hemophilia B Rat Model—Introduction The present specification provides a composition for engineering F9 gene. One embodiment of the disclosure of the present application relates to a composition for artificial engineering or modifying F9 gene.

Composition for Producing Hemophilia B Rat Model—Example

The composition for engineering or modifying F9 gene may include the aforementioned engineered nuclease or a nucleic acid encoding the engineered nuclease. For example, the engineered nuclease can be one or more of TALEN, ZFN, meganuclease, and CRISPR-enzyme.

The composition for engineering F9 gene may include an antisense RNA capable of forming a complementary bond with partial nucleotide sequence in F9 gene, for example, siRNA, shRNA, or the like.

The composition for engineering or modifying F9 gene or a gene encoding the same may include dominant negative mutant F9, ribozyme, or the like.

Alternatively, in another embodiment of the disclosure of the present application, the composition may include one or more of dominant negative mutant, intracellular antibody, peptide and small molecule which inhibit or suppress the function of F9 protein.

The composition may include one or more guide RNA and Cas9 enzyme or a complex thereof, one or more of antisense RNA and dominant negative mutant F9 factor as a mixture.

The composition can be provided in form of an expression cassette.

Composition Comprising CRISPR—Cas System; 1-Introduction

One embodiment of the disclosure of the present application relates to, as a composition for engineering F9 gene, a composition comprising CRISPR-Cas system.

In one embodiment disclosed in the present application, the composition may comprise a guide RNA or a DNA encoding the guide RNA; and an editor protein or a DNA encoding the editor protein, and the editor protein is CRISPR enzyme, which is the same as defined above.

In one embodiment, the CRISPR enzyme can be Cas9 protein originating from *Streptococcus pyogenes.*

In one embodiment, the guide RNA may have homology with the target sequence in F9 gene, or may form a complementary bond with the target sequence.

Once a guide RNA-editor protein complex binds to F9 gene or nucleotide sequence of F9 gene, the F9 gene or nucleotide sequence of F9 gene can be cleaved or modified by the editor protein in the guide RNA-editor protein complex.

Composition Comprising CRISPR-Cas System; 2—Target Sequence of Guide RNA

The composition comprising CRISPR Cas system comprises a guide RNA. The guide RNA has homology with the target sequence, or the guide RNA has a sequence which can form a complementary bond with the target sequence. Hereinbelow, the target sequence is explained in detail.

"Target sequence" refers to a nucleotide sequence located in a target gene or target nucleic acid, and specifically, target sequence is a partial nucleotide sequence in target region in a target gene or target nucleic acid. Herein, "target region" refers to a region that can be modified by a guide nucleic acid-editor protein in a target gene or target nucleic acid.

Hereinbelow, the target sequence can be used as a term meaning all sequence information of the two nucleotide sequences. For example, in case of a target gene, the target sequence may refer to the nucleotide sequence information of a transcribed strand or the nucleotide sequence information of a non-transcribed strand in a target gene DNA.

In one example, the target gene can be F9 gene.

In one embodiment, the target sequence in F9 gene can be a continuous 10 to 35-nucleotide sequence located in the exon region in F9 gene.

In that case, the target sequence can be 10 to 35-nucleotide sequence, 15 to 35-nucleotide sequence, 20 to 35-nucleotide sequence, 25 to 35-nucleotide sequence, or 30 to 35-nucleotide sequence.

Alternatively, the target sequence can be 10 to 15-nucleotide sequence, 15 to 20-nucleotide sequence, 20 to 25-nucleotide sequence, 25 to 30-nucleotide sequence, or 30 to 35-nucleotide sequence.

The target sequence in F9 gene can be a continuous 10 to 35-nucleotide sequence located in the promoter region in F9 gene.

In that case, the target sequence can be 10 to 35-nucleotide sequence, 15 to 35-nucleotide sequence, 20 to 35-nucleotide sequence, 25 to 35-nucleotide sequence or 30 to 35-nucleotide sequence.

Alternatively, the target sequence can be 10 to 15-nucleotide sequence, 15 to 20-nucleotide sequence, 20 to 25-nucleotide sequence, 25 to 30-nucleotide sequence, or 30 to 35-nucleotide sequence.

The target sequence in F9 gene can be a continuous 10 to 35-nucleotide sequence located in the intron region in F9 gene.

In that case, the target sequence can be 10 to 35-nucleotide sequence, 15 to 35-nucleotide sequence, 20 to 35-nucleotide sequence, 25 to 35-nucleotide sequence or 30 to 35-nucleotide sequence.

Alternatively, the target sequence can be 10 to 15-nucleotide sequence, 15 to 20-nucleotide sequence, 20 to 25-nucleotide sequence, 25 to 30-nucleotide sequence, or 30 to 35-nucleotide sequence.

The target sequence in F9 gene can be a continuous 10 to 35-nucleotide sequence located in the enhancer region in F9 gene.

In that case, the target sequence can be 10 to 35-nucleotide sequence, 15 to 35-nucleotide sequence, 20 to 35-nucleotide sequence, 25 to 35-nucleotide sequence or 30 to 35-nucleotide sequence.

Alternatively, the target sequence can be 10 to 15-nucleotide sequence, 15 to 20-nucleotide sequence, 20 to 25-nucleotide sequence, 25 to 30-nucleotide sequence, or 30 to 35-nucleotide sequence.

The target sequence in F9 gene can be a continuous 10 to 35-nucleotide sequence located in the promoter, enhancer, 3' UTR, polyadenyl (polyA) or a mixed part thereof in F9 gene.

In that case, the target sequence can be 10 to 35-nucleotide sequence, 15 to 35-nucleotide sequence, 20 to 35-nucleotide sequence, 25 to 35-nucleotide sequence or 30 to 35-nucleotide sequence.

Alternatively, the target sequence can be 10 to 15-nucleotide sequence, 15 to 20-nucleotide sequence, 20 to 25-nucleotide sequence, 25 to 30-nucleotide sequence, or 30 to 35-nucleotide sequence.

The target sequence in F9 gene can be a continuous 10 to 35-nucleotide sequence located in the exon, intron, or a mixed part thereof in F9 gene.

In that case, the target sequence can be 10 to 35-nucleotide sequence, 15 to 35-nucleotide sequence, 20 to 35-nucleotide sequence, 25 to 35-nucleotide sequence or 30 to 35-nucleotide sequence.

Alternatively, the target sequence can be 10 to 15-nucleotide sequence, 15 to 20-nucleotide sequence, 20 to 25-nucleotide sequence, 25 to 30-nucleotide sequence, or 30 to 35-nucleotide sequence.

The target sequence in F9 gene can be a continuous 10 to 35-nucleotide sequence which includes a mutation part in F9 gene (e.g., part different from the wild type) or adjacent thereto.

"Mutation" is a modification occurred in nucleotide sequence of DNA of a gene, and it includes all modifications resulting from deletion, insertion, or substitution of one or more nucleotides in the nucleotide sequence of DNA included in the gene. The sequence having a mutation occurred in a gene is referred to as a "mutation sequence". In addition, the mutation includes all modifications resulting from deletion, insertion, or substitution of some amino acids of a protein encoded by a gene, which is caused by mutation in the gene.

Herein, one or more mutations can be a mutation which is caused naturally.

Herein, one or more mutations can be a synonymous mutation which does not exhibit any effect on the expression of a subject protein.

For example, when the subject is a gene dependent on single nucleotide polymorphism, one or more mutations can be a mutation which does not exhibit any effect on drug response, side effects, or drug resistance with regard to a specific disease (cancer, diabetes, high blood pressure, or the like).

In that case, the target sequence can be 10 to 35-nucleotide sequence, 15 to 35-nucleotide sequence, 20 to 35-nucleotide sequence, 25 to 35-nucleotide sequence or 30 to 35-nucleotide sequence.

Alternatively, the target sequence can be 10 to 15-nucleotide sequence, 15 to 20-nucleotide sequence, 20 to 25-nucleotide sequence, 25 to 30-nucleotide sequence, or 30 to 35-nucleotide sequence.

Preferably, the target sequence disclosed in the present specification can be a continuous 10 to 35-nucleotide sequence which is located in the exon region or exon, intron, or a mixed part thereof in F9 gene.

In that case, the target sequence can be 10 to 35-nucleotide sequence, 15 to 35-nucleotide sequence, 20 to 35-nucleotide sequence, 25 to 35-nucleotide sequence or 30 to 35-nucleotide sequence.

Alternatively, the target sequence can be 10 to 15-nucleotide sequence, 15 to 20-nucleotide sequence, 20 to 25-nucleotide sequence, 25 to 30-nucleotide sequence, or 30 to 35-nucleotide sequence.

The target sequence in F9 gene can be a continuous 10 to 35-nucleotide sequence which is adjacent to the 5' terminus and/or 3' terminus of PAM (proto-spacer-adjacent motif) sequence in the nucleotide sequence of F9 gene.

Herein, the PAM sequence can be one or more of the following sequences (described in direction of from 5' to 3')

NG (N is A, T, C or G);

NGG (N is A, T, C or G);

NNNNRYAC (N is, each independently, A, T, C or G, R is A or G, and Y is C or T);

NNAGAAW (N is, each independently, A, T, C or G, and W is A or T);

NNNNGATT (N is, each independently, A, T, C or G);

NNGRR (T) (N is, each independently, A, T, C or G, and R is A or G); and

TTN (N is A, T, C or G).

In one example, the PAM sequence can be NGG (N is A, T, C or G).

In one example, the target sequence can be one or more sequences selected from the group consisting of SEQ ID NOs: 1 to 6. In one example, the guide RNA may have homology with one or more target sequences selected from the group consisting of SEQ ID NOs: 1 to 6, or the guide RNA may include a sequence which can form a complementary bond with the target sequences.

Composition Comprising CRISPR-Cas System; 3—Whole Sequence of Guide RNA

The guide RNA further comprises a sequence portion capable of forming a complex with Cas9 protein as well as a sequence which has homology with the target sequence described above or a sequence capable of forming a complementary bond with the target sequence. The sequence portion may vary depending on the origin of Cas9 protein. In one example, when the CRISPR-Cas system includes an editor protein which is Cas9 protein originating from *Streptococcus pyogenes*, the guide RNA may include a target sequence and a sequence portion expressed by 5'-GUUUUAGAGCUA-GAAAUAGCAAGUUAAAAUAAGGCUAGU-CCGUUAUCAAC UUGAAAAAGUGGCACCGAGUCG-GUGC-3' (SEQ ID NO: 27). In one example, when the CRISPR-Cas system includes an editor protein which is Cas9 protein originating from *Campylobacter jejuni*, the guide RNA may include a target sequence and a sequence portion expressed by 5'-GUUUUAGUCC-CUGAAAAGGGACUAAAAUAAAGAGUUUGCGGGA-CUCUGCG GGGUUACAAUCCCUAAAACCGC-UUUU-3' (SEQ ID NO: 28). In one example, the guide RNA may include a sequence selected from the group consisting of SEQ ID NOs: 21 to 26.

Composition Comprising CRISPR-Cas System; 4—Editor Protein

The composition comprising CRISPR-Cas system comprises an editor protein. Function of the editor protein has been described above. In one embodiment, the editor protein can be one or more selected from the group consisting of Cas9 protein originating from *Streptococcus pyogenes*, Cas9 protein originating from *Campylobacter jejuni*, Cas9 protein originating from *Streptococcus thermophilus*, Cas9 protein originating from *Staphylococcus aureus*, and Cas9 protein originating from *Neisseria meningitidis*. In a preferred embodiment, the editor protein can be Cas9 protein originating from *Streptococcus pyogenes*.

Composition Comprising CRISPR-Cas System; 5—Guide Nucleic Acid-Editor Protein Complex Explanations of the guide nucleic acid and the editor protein are the same as described above.

The guide nucleic acid, which capable of forming a complementary bond with F9 gene, and the editor protein can form a guide nucleic acid-editor protein complex.

The guide nucleic acid-editor protein complex can be formed outside a cell.

The guide nucleic acid-editor protein complex can be formed in a cytoplasm in a cell.

The guide nucleic acid-editor protein complex can be formed in a nucleus in a cell.

In the guide nucleic acid-editor protein complex, the editor protein may recognize PAM located in F9 gene or nucleotide sequence in F9 gene.

In guide nucleic acid-editor protein complex, the guide nucleic acid can form a complementary bond with F9 gene or nucleotide sequence in F9 gene.

Once the guide nucleic acid-editor protein complex binds to F9 gene or nucleotide sequence in F9 gene, the F9 gene or the nucleotide sequence can be cleaved or modified by the editor protein in the guide nucleic acid-editor protein complex.

Composition Comprising CRISPR-Cas System; 6—In Form of CRISPR-Cas System

In the composition, the CRISPR-Cas system can be comprised in form of a viral vector, a non-viral vector, or a non-vector.

In one example, the CRISPR-Cas system can be present in form of RNP (ribonucleoprotein) in which the guide RNA and CRISPR enzyme form a complex.

In another example, the CRISPR-Cas system can be included in vector in form of a nucleic acid.

The vector can be a viral vector or a non-viral vector.

The CRISPR-Cas system can be included in one vector.

The CRISPR-Cas system can be included in two or more vectors. In that case, the two vectors may a vector of the same kind or a vector of different kind.

Method of Producing Rat Cell Including Artificially
Modified F9 Gene

Method of Producing Rat Cell Including Artificially Modified F9 Gene—Introduction One embodiment of the present invention relates to a method of producing rat cell including artificially modification in F9 gene. In one example, the production method includes contacting a rat cell with the composition for modifying F9 gene. Furthermore, the production method may further include culturing transformed cells; and/or sorting the transformed cells.

Contacting with Composition for Gene Modification

The method of producing includes, as a critical constitutional element, artificially modifying F9 gene of a rat cell. Herein, the aforementioned composition for engineering F9 gene can be used.

In one embodiment, the method of producing may include contacting a rat cell with the composition for engineering F9 gene. In one embodiment, the rat cell can be a somatic cell, an embryonic cell, or an embryonic stem cell. In one embodiment, the contacting can be performed by one or more methods selected from electroporation, a method of using liposome, plasmid, viral vector, or nanoparticles, and PTD (protein translocation domain) fusion protein method. In one embodiment, the contacting can be performed in vitro.

Culturing Transformed Cells

The transformed cells using the genetic engineering technology can form a colony. The cell colony including transformed cells is the same as described above.

Rat-derived cells transformed with a recombinant expression vector for artificial modification of the F9 gene can be proliferated and cultured by methods well known in the art.

Suitable culture medium can be developed for culture of animal cells, in particular, rodent animal cells, or any usable culture medium which can be produced in a lab with suitable components required for growth of animal cells such as anabolic carbon, nitrogen, and/or trace nutrients can be used.

The culture medium may be any basic culture medium suitable for growth of animal cells. As a non-limiting example, the basic culture medium, generally used for culture, may be MEM (Minimal Essential Medium), DMEM (Dulbecco Modified Eagle Medium), RPMI (Roswell Park Memorial Institute Medium), and K-SFM (Keratinocyte Serum Free Medium). In addition, any culture medium used in the art can be used without limitation. Preferably, the culture medium can be selected from the group consisting of α-MEM medium (GIBCO), K-SFM medium, DMEM medium (Welgene), MCDB 131 medium (Welgene), IMEM medium (GIBCO), DMEM/F12 medium, PCM medium, M199/F12 (mixture) (GIBCO), and MSC medium (Chemicon).

To those basic culture medium, may be added anabolic source of carbon, nitrogen, and trace nutrients. As a non-limiting example, the source may be a serum source, growth factor, amino acid, antibiotic, vitamin, reducing agent, and/or a sugar source.

It is obvious that a skilled person in the art can select or combine appropriate culture mediums and perform culture suitably by known methods. Also, it is obvious that, based on common knowledge in the art, the culture can be performed with controlled conditions, such as an environment suitable for culture, time, temperature, or the like.

Sorting Transformed Cells

Another embodiment of the present application may include a step of sorting transformed cells including F9-targeted genetic engineering technology.

Herein, the transformed cells can be sorted from a colony by using one or more antibiotic resistance gene, antigen-antibody reaction, fluorescent protein, and surface marker gene.

For example, cells, which comprise F9-targeted genetic engineering technology, e.g., guide RNA and Cas9 protein, can be identified by a fluorescence signal. Thus, they can be distinguished from cells not comprising the genetic engineering technology described above.

Method of Producing Hemophilia B Rat Model

Method for Producing Hemophilia B Rat Model—Introduction

The present specification provides a method of producing a hemophilia B rat model. In one example, the method of producing can be a method of producing a rat with engineered F9 gene by using CRISPR/Cas system. In another example, the method of producing can be a method of producing a rat with engineered F9 gene by using embryonic cell transplantation. In still another example, the method of producing can be a method of producing a rat with engineered F9 gene by using nuclear donor cell. Method of producing rat with engineered F9 gene by using embryonic cell transplantation One embodiment described in the present specification relates to a method of producing a rat with engineered F9 gene by using embryonic cell transplantation.

The method may include (a) contacting an embryonic cell isolated from tissues of rat with the aforementioned composition for engineering F9 gene;

(b) transplanting the embryos into a surrogate mother; and (d) allowing the surrogate mother to be pregnant with a rat having artificially modified F9 gene.

Details of common technologies for each step can be understood in view of conventional methods for embryo transplant which is known in the art.

Furthermore, with the step of contacting the composition for engineering F9 gene can use conventional methods known in the art.

For example, the composition for engineering F9 gene, comprising a guide RNA-Cas9 complex formed in vitro, can be contacted with an embryonic cell by using known methods such as electroporation or microinjection.

In another example, the composition for engineering F9 gene can be introduced to a cell by using one or more vectors and the composition can bind to a target sequence of F9 gene by forming a complex in cell.

Method of Producing Rat with Engineered F9 Gene by Using Nuclear Donor Cell

One embodiment disclosed in the present specification relates to a method of producing a transformed rat as hemophilia B model in which F9 gene is artificially knocked out, by the method including: transplanting of a nucleus from a nuclear donor cell, which has been introduced a recombinant vector into a denucleated oocyte; and producing a rat offspring, and the embodiment also relates to a rat as hemophilia B model produced by the method.

In a specific embodiment, a hemophilia B rat is produced by using the transformed cell line in which F9 gene is artificially knocked out, and a method of somatic cell nuclear transfer (SCNT).

The production method may include (a) producing a nuclear donor cell including culturing somatic cells or stems cells isolated from tissues of rat;

(b) contacting the nuclear donor cell with the composition for engineering F9 gene;

(c) producing a denucleated oocyte by removing the nucleus from rat oocyte, (d) microinjecting the nuclear donor cell of the step (b) into the denucleated oocyte of the step (c) and fusing them;

(e) activating the oocyte which has been fused in the step (d); and (f) transplanting the activated oocyte into an oviduct of a surrogate mother.

Details of a common technology for each step can be understood in view of conventional methods for producing a clone animal by using somatic nuclear transfer technology that is well known in the art.

Animal Model for Study and/or Treatment of Hemophilia B

The present specification provides an animal model for study and/or treatment of hemophilia B by using a novel hemophilia B rat which does not exist before.

The hemophilia B rat can be used for investigation of the cause and/or mechanism of hemophilia B, study of the disease symptoms, search for therapeutic agents, or the like.

The hemophilia B rat as an animal disease model exhibits a pathological mechanism similar to a human patient with hemophilia B, and thus it is very useful as an animal model for study of the treatment of human hemophilia B.

In one embodiment of the present application, an animal model for screening pharmaceuticals for treatment of hemophilia B can be provided by using the novel hemophilia B rat which does not exist before. More particularly, an animal model for screening pharmaceuticals for prevention or treatment of spontaneous bleeding of hemophilia B can be provided.

Figures 4A, 4B, 4C:
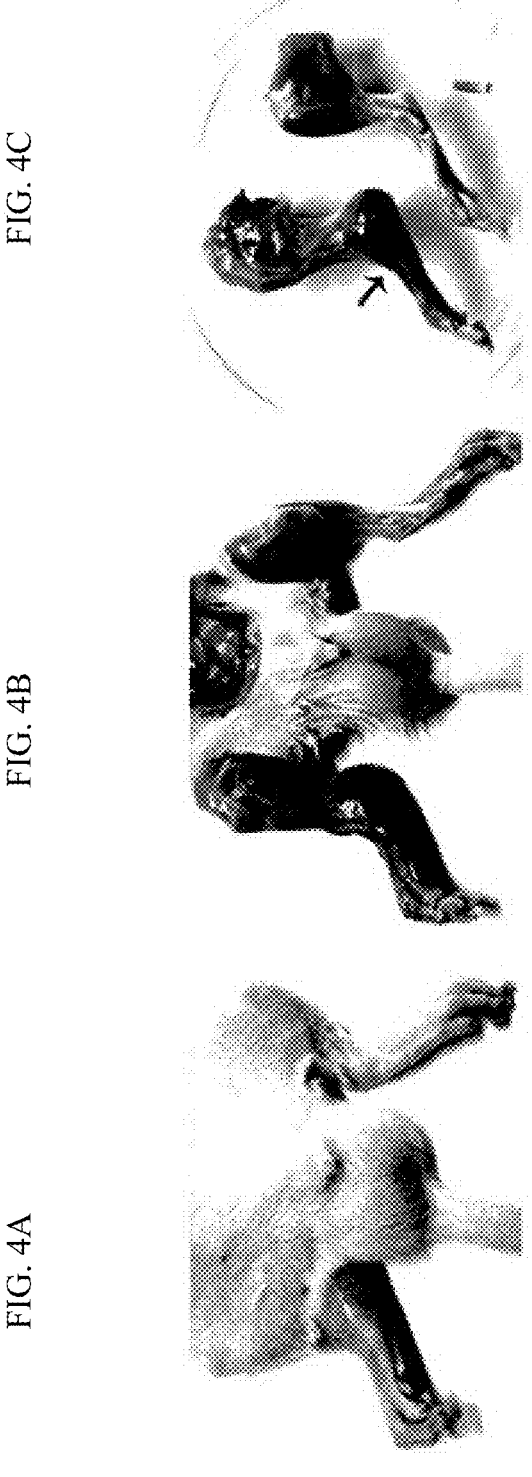
FIGS. 4A-4C are photographic images illustrating the spontaneous bleeding phenomenon occurring in a rat with knock-out F9 gene.
Figure 5:
FIG. 5 is a photographic image illustrating the symptom exhibited on paw pad of a rat with knock-out F9 gene.
Figure 6:
FIG. 6 is a photographic image illustrating the symptom exhibited on an eye of a rat with knock-out F9 gene.
Figures 7A, 7B, 7C, 7D:
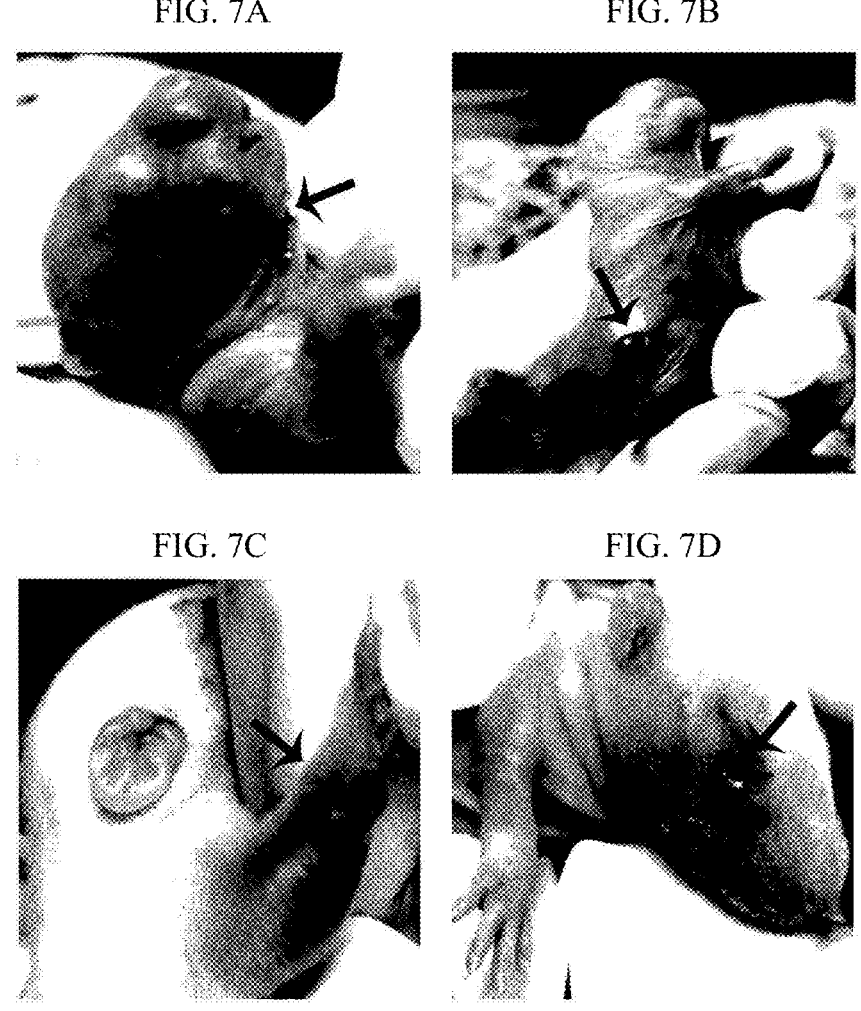
FIGS. 7A-7D are photographic images illustrating the symptom exhibited in a baby rat offspring with knock-out F9 gene.

The rat model in the present application can exhibit the symptoms of: spontaneous bleeding in the knee joint, muscle, eye, or the like; and swelling or inflammation by spontaneous bleeding. The symptoms can be caused by artificially modifying the F9 gene, and thus by reduced or lost the expression of F9 protein, and/or by hypofunction or loss-of-function of the F9 protein. For example, FIGS. 4A-4C are photographic images illustrating the spontaneous bleeding phenomenon occurring in a rat with knock-out F9 gene. FIG. 4A shows severe swelling and discoloration of the hindlimb joint associated with extensive spontaneous subcutaneous and intramuscular bleeding, which mimics the spontaneous joint hemorrhages (hemarthrosis) commonly observed as a clinical manifestation of hemophilia B, FIG. 4B shows the same hindlimb with the skin removed, demonstrating extensive accumulation of blood (hematoma) within the muscle and periarticular tissue, paralleling the deep tissue and soft tissue bleeds typical in hemophilia B patients, and FIG. 4C shows wherein the arrow indicates the sites of spontaneous hemorrhage characteristic of F9 deficiency and reflective of the bleeding diathesis seen in human hemophilia B. FIG. 5 is a photographic image illustrating the symptom exhibited on paw pad of a rat with knock-out F9 gene. FIG. 6 is a photographic image illustrating the symptom exhibited on an eye of a rat with knock-out F9 gene. FIGS. 7A-7D are photographic images illustrating the symptom exhibited in a baby rat offspring with knock-out F9 gene. FIG. 7A shows marked swelling and discoloration of the scalp area, wherein the arrow indicates spontaneous subcutaneous hemorrhage, which parallels the soft tissue and scalp hematomas often seen in neonates with severe hemophilia B, FIG. 7B shows hemorrhagic infiltration and edema localized to the lateral abdominal wall, wherein the arrow indicates bleeding into the soft tissues and muscles of the flank and abdomen, which corresponds to subcutaneous and intramuscular hematomas often observed in severe hemophilia B patients, typically presenting as painful swelling and bruising without obvious trauma, FIG. 7C shows extensive bruising and swelling of the forelimb, wherein the arrow indicates spontaneous intramuscular or deep tissue hematoma, reflecting the typical presentation of recurrent bleeding episodes in infants with untreated or severe hemophilia B, and FIG. 7D shows periorbital swelling, wherein the arrow indicates periocular or subconjunctival hemorrhage, which, although rare, is a documented extra-articular bleeding complication in hemophilia B.

Thus, the hemophilia B rat is very useful as an animal model for screening a therapeutic agent, i.e., pharmaceuticals, for hemophilia B. That is, the hemophilia B rat can confirm whether hemophilia B is induced, and by administering a therapeutic agent being developed currently into the rat, the rat can be used in various applications such as the investigation of the mechanism of hemophilia B, the search of therapeutic agent, and the development of diagnostic methods.

In one embodiment, the method for screening pharmaceuticals for hemophilia B may include:

(a) administering a candidate material for palliating, preventing, or treating hemophilia B into a hemophilia B rat; and (b) after administering the candidate material, performing comparative analysis in view of a control which has not been administered with any candidate material.

Preferably, the candidate material may be at least one selected from the group consisting of a peptide, a protein, a non-peptide compound, a synthetic compound, a fermentation product, a cell extract, a plant extract, and an extract from animal tissue, but it is not limited thereto.

The compound can be either a novel compound or a publicly known compound. Herein, the compound may form a salt.

Administration of a candidate material in the above step (b) can be performed by any convenient method like injection, transfusion, implantation, and transplantation. Route for the administration can be selected from subcutaneous, intradermal, intratumoral, intranodal, intramedullar, intramuscular, intravenous, intralymphatic, and intraperitoneal administration, but it is not limited thereto. The candidate material can be administered in a rat according to suitable dosage, administration method, or properties of a candidate material.

DESCRIPTION OF SPECIFIC EMBODIMENTS FOR CARRYING OUT INVENTION

The following examples are given only for more specific explanation of the present invention, and it would be obvious to a skilled person in the art of the present invention that the scope of present invention should not be limited by the examples.

1. gRNA Design

By using CRISPR RGEN Tools (Park et al, Bioinformatics 31:4014-4016, 2015), a guide RNA considering six "NGG"PAM, which correspond to Exon 1 and Exon 2 of rat F9 gene (ENSRNOG00000003430.7), was designed. For the designed guide RNA, absence of 1 base or 2 base mismatch except the on-target site on rat genome was taken into consideration.

TABLE 1

| Target DNA sequence of guide RNA for rat F9 gene KO (knock-out) | | |
|---|---|---|
| sgRNA | Target | SEQ ID NO |
| Rat_F9_Exon1_gRNA1_target DNA | GCCATCATGGCAGACGCTCC | SEQ ID NO: 1 |
| Rat_F9_Exon1_gRNA2_target DNA | TGCTGAGTAGATAGCCCAGA | SEQ ID NO: 2 |
| Rat_F9_Exon2_gRNA3_target DNA | TGGACGGGTAAGAATTTTGG | SEQ ID NO: 3 |
| Rat_F9_Exon2_gRNA4_target DNA | CTTTGGACGGGTAAGAATTT | SEQ ID NO: 4 |
| Rat_F9_Exon2_gRNA5_target DNA | TGAGTTATATCTCTTTGGAC | SEQ ID NO: 5 |
| Rat_F9_Exon2_gRNA6_target DNA | CGTCCAAAGAGATATAACTC | SEQ ID NO: 6 |

Deep sequencing primers used for determining, in an embryo pool, indels generated by the 6 guide RNAs are described below.

TABLE 2

| Deep sequencing primers for determining on-target editing with regard to guide RNA | | |
|---|---|---|
| Primer name | Sequence | SEQ ID NO |
| Rat-F9_exon1_F | CTTTCCTGACAGCAGCACAA | SEQ ID NO: 7 |
| Rat-F9_exon1_R | ATGCACCGCAAACACTGTAA | SEQ ID NO: 8 |
| Rat-F9_exon2_F | AGGGAATGACGATCACCTTG | SEQ ID NO: 9 |
| Rat-F9_exon2_R | TTGACGTTTTCCATCTTTTGC | SEQ ID NO: 10 |
| Rat_F9_exon1_2nd_F | ACACTCTTTCCCTACACGACGCTCTTCCGA TCTCCCATTCAGCTTGTACTTTGG | SEQ ID NO: 11 |
| Rat_F9_exon1_2nd_R | GTGACTGGAGTTCAGACGTGTGCTCTTCCG ATCTGACATGCTGCCTGCTACAAT | SEQ ID NO: 12 |
| Rat_F9_exon2_2nd_F | ACACTCTTTCCCTACACGACGCTCTTCCGA TCTCCCAAAGAGAAATTAGCTATGGAA | SEQ ID NO: 13 |
| Rat_F9_exon2_2nd_R | GTGACTGGAGTTCAGACGTGTGCTCTTCCG ATCTTCGTGCTTCTTCAAAACTGC | SEQ ID NO: 14 |

F: forward primer,
R: reverse primer

2. Synthesis of gRNA

For transfer system based on RNP, sgRNA was transcribed by T7 RNA polymerase after forming a template by annealing between two partial oligonucleotides (Forward primer: GAAATTAATACGACTCACTATAGCGTC-CAAAGAGATATAACTCAGGGTTTTA GAGCTAGAAATAGC (SEQ ID NO: 29), Reverse primer: AAAAAAAGCACCGACTCGGTGCCACTTTTT-CAAGTTGATAACGGACTAGCCTT ATTTTAACTTGC-TATTTCTAGCTCTAAAAC (SEQ ID NO: 30)) which have been produced by Phusion-mediated polymerization. The transcribed sgRNA was purified and quantified by using spectrometry.

Sequence of the synthesized sgRNA is described below.

TABLE 3

| Guide RNA synthesis sequence for rat F9 gene KO | | |
|---|---|---|
| Name | sgRNA Synthesis sequence | SEQ ID NO |
| Rat_F9_Exon1_gRNA1_synthesis seq | GAAATTAATACGACTCACTATAGGCCATCATG GCAGACGCTCCGTTTTAGAGCTAGAAATAGC | SEQ ID NO: 15 |
| Rat_F9_Exon1_gRNA2_synthesis seq | GAAATTAATACGACTCACTATAGTGCTGAGTA GATAGCCCAGAGTTTTAGAGCTAGAAATAGC | SEQ ID NO: 16 |
| Rat_F9_Exon2_gRNA3_synthesis seq | GAAATTAATACGACTCACTATAGTGGACGGGT AAGAATTTTGGGTTTTAGAGCTAGAAATAGC | SEQ ID NO: 17 |
| Rat_F9_Exon2_gRNA4_synthesis seq | GAAATTAATACGACTCACTATAGCTTTGGACG GGTAAGAATTTGTTTTAGAGCTAGAAATAGC | SEQ ID NO: 18 |

TABLE 3-continued

Guide RNA synthesis sequence for rat F9 gene KO

| Name | sgRNA Synthesis sequence | SEQ ID NO |
|------|--------------------------|-----------|
| Rat_F9_Exon2_gRNA5_synthesis seq | GAAATTAATACGACTCACTATAGTGAGTTATA TCTCTTTGGACGTTTTAGAGCTAGAAATAGC | SEQ ID NO: 19 |
| Rat_F9_Exon2_gRNA6_synthesis seq | GAAATTAATACGACTCACTATAGCGTCCAAAG AGATATAACTCGTTTTAGAGCTAGAAATAGC | SEQ ID NO: 20 |

TABLE 4

Guide RNA for rat F9 gene KO

| Name | sgRNA Synthesis sequence | SEQ ID NO |
|------|--------------------------|-----------|
| Rat_F9_Exon1_gRNA1 | GCCAUCAUGGCAGACGCUCCGUUUUAGAGCUAGAAA UAGCAAGUUAAAAUAAGGCUAGUCCGUUAUCAACUU GAAAAAGUGGCACCGAGUCGGUGC | SEQ ID NO: 21 |
| Rat_F9_Exon1_gRNA2 | UGCUGAGUAGAUAGCCCAGAGUUUUAGAGCUAGAAA UAGCAAGUUAAAAUAAGGCUAGUCCGUUAUCAACUU GAAAAAGUGGCACCGAGUCGGUGC | SEQ ID NO: 22 |
| Rat_F9_Exon2_gRNA3 | UGGACGGGUAAGAAUUUUGGGUUUUAGAGCUAGAAA UAGCAAGUUAAAAUAAGGCUAGUCCGUUAUCAACUU GAAAAAGUGGCACCGAGUCGGUGC | SEQ ID NO: 23 |
| Rat_F9_Exon2_gRNA4 | CUUUGGACGGGUAAGAAUUUGUUUUAGAGCUAGAAA UAGCAAGUUAAAAUAAGGCUAGUCCGUUAUCAACUU GAAAAAGUGGCACCGAGUCGGUGC | SEQ ID NO: 24 |
| Rat_F9_Exon2_gRNA5 | UGAGUUAUAUCUCUUUGGACGUUUUAGAGCUAGAAA UAGCAAGUUAAAAUAAGGCUAGUCCGUUAUCAACUU GAAAAAGUGGCACCGAGUCGGUGC | SEQ ID NO: 25 |
| Rat_F9_Exon2_gRNA6 | CGUCCAAAGAGAUAUAACUCGUUUUAGAGCUAGAAA UAGCAAGUUAAAAUAAGGCUAGUCCGUUAUCAACUU GAAAAAGUGGCACCGAGUCGGUGC | SEQ ID NO: 26 |

3. Establishment (selection) of F9−/− rat

By using Rat_F9_Exon2_gRNA4 of Table 1, it was determined whether or not an indel is formed in Exon 2 region of F9 gene.

TABLE 5

Determination of indel in Exon 2 region of F9 gene

| Type | Sequence |
|------|----------|
| WT | ACTTTCAAATTTCAGTTTTTCTTGATCGCGAAAATGCACCAAA ATTCTTACCCGTCCAAAGAGATATAACTCAGGGAAACTGGAAG AGTTTGTTCAGGGAAACCTTGAGA (SEQ ID NO: 31) |
| WT-2 | ACTTTCAAATTTCAGTTTTTCTTGATCGCGAAAATGCACCAAA ATTCTTACCCGTCCAAAGAGATATA--TCAGGGAAACTGGAAG AGTTTGTTCAGGGAAACCTTGAGA (SEQ ID NO: 32) |
| WT | ACTTTCAAATTTCAGTTTTTCTTGATCGCGAAAATGCACCAAA ATTCTTACCCGTCCAAAGAGATATAACTCAGGGAAACTGGAAG AGTTTGTTCAGGGAAACCTTGAGA (SEQ ID NO: 31) |
| WT-35 | ACTTTCAAATTTCAGTTTTTCTTGATCGCGAAAATG------- ------------------------------------------- --CAGGGAAACTGGAAGAGTTTGTTCAGGGAAACCTTGAGA (SEQ ID NO: 33) |
| WT | ACTTTCAAATTTCAGTTTTTCTTGATCGCGAAAATGCACCAAA ATTCTTACCCGTCCAAAGAGATATAACTCAGGGAAACTGGAAG AGTTTGTTCAGGGAAACCTTGAGA (SEQ ID NO: 31) |

TABLE 5-continued

Determination of indel in Exon 2 region of F9 gene

| Type | Sequence |
|------|----------|
| WT-4 | ACTTTCAAATTTCAGTTTTTCTTGATCGCGAAAATGCACCAAA ATTCTTACCCGTCCAAAGAGATA----TCAGGGAAACTGGAAG AGTTTGTTCAGGGAAACCTTGAGA (SEQ ID NO: 34) |
| WT | ACTTTCAAATTTCAGTTTTTCTTGATCGCGAAAATGCACCAAA ATTCTTACCCGTCCAAAGAGATATAACTCAGGGAAACTGGAAG AGTTTGTTCAGGGAAACCTTGAGA (SEQ ID NO: 31) |
| WT + 4, T->A | ACTTTCAAATTTCAGTTTTTCTTGATCGCGAAAATGCACCAAA ATTCTTACCCGTCCAAAGAGATATAACAACAATCAGGGAAACT GGAAGAGTTTGTTCAGGGAAACCTTGAGA (SEQ ID NO: 35) |
| WT-4 | ACTTTCAAATTTCAGTTTTTCTTGATCGCGAAAATGCACCAAA ATTCTTACCCGTCCAAAGAGATA----TCAGGGAAACTGGAAG AGTTTGTTCAGGGAAACCTTGAGA (SEQ ID NO: 34) |
| WT | ACTTTCAAATTTCAGTTTTTCTTGATCGCGAAAATGCACCAAA ATTCTTACCCGTCCAAAGAGATATAACTCAGGGAAACTGGAAG AGTTTGTTCAGGGAAACCTTGAGA (SEQ ID NO: 31) |

TABLE 5-continued

Determination of indel in Exon 2 region of F9 gene

| Type | Sequence |
|------|----------|
| WT-2 | ACTTTCAAATTTCAGTTTTTCTTGATCGCGAAAATGCACCAAA ATTCTTACCCGTCCAAAGAGATATA--TCAGGGAAACTGGAAG AGTTTGTTCAGGGAAACCTTGAGA (SEQ ID NO: 32) |

-: Sequence deleted,
underlined: sequence inserted,
bold: sequence substituted

4. Production of F9−/− rat

By transplanting in a surrogate a fertilized egg having F9 gene knocked out using CRISPR/Cas9, a cloned embryo was produced.

More specific explanations are given in the followings.

4-1. Hormone Administration and Harvesting Fertilized Egg

By administering, at 11 AM of Day-3, PMSG-Daesung Microbiological Labs, Co., Ltd. (15 IU) to a 5 week-old female rat for egg harvesting, luteinizing hormone was synchronized. At 11 AM of Day-1, hCG-Daesung Microbiological Labs, Co., Ltd. (15 IU) was administered to the female for egg harvesting to synchronize the ovulation day. After that, the female was allowed to mate a WT male rat. At 9 AM of the next day (Day-0), vaginal plug was checked, and then only the oviduct was separately collected with caution while holding a part connecting the ovary-oviduct-womb.

Thirty minutes before collecting an egg, M2 medium-SIGMA (medium for washing) and mR1ECM-ark-resource (culture medium for rat-4 drops (100 µl for each drop) are formed and covered with paraffin oil) are prepared in advance in an incubator. Within 30 seconds after starting anesthetizing the rat, M2 medium was removed and the fertilized egg was collected by tearing the ampulla of oviduct under microscope. After that, 4 drops of M2 medium (100 µl for each drop) were prepared and used in turn for washing, and also 4 drops of mR1ECM medium (100 µl for each drop) were prepared and used in turn for washing. The fertilized egg obtained after washing was quickly transferred to an incubator with mRIECM medium (100 µl, covered with paraffin oil), which has been prepared in advance, to give a stable period.

4-2. Transfection

The fertilized egg was removed from the incubator and washed with 4 drops of mR1ECM medium (100 µl for each drop) followed by washing with 4 drops of M2 medium (100 µl for each drop). After that, to have electroporation (BEX-Gene editor1) of sgRNA:Cas9 protein/8 into the fertilized egg, sgRNA:Cas9 protein/8 were mixed at a ratio of 0 µg: 320 µg, incubated for 15 minutes, and used. For the electroporation, 1 cell (40 pieces) was used per gun, and the electroporation was carried out at conditions of Pd: 30 V, Pd on: 3.00 ms, Pd off: 97.0 ms, Pd cycle: 7.

After the electroporation of the fertilized egg, the fertilized egg obtained upon the completion of the electroporation was washed with 4 drops of M2 medium (100 µl for each drop) followed by washing with 4 drops of mRIECM medium (100 µl for each drop). Then, the egg was transferred to mRIECM medium prepared in advance in an incubator and cultured. The process was repeatedly carried out (with medium for rat culture-4 drops (100 µl for each drop) are prepared and covered with paraffin oil). Upon the completion of the all electroporation, the fertilized egg added in mRIECM medium was cultured for a day.

4-3. Transplant of Fertilized Egg

At AM 11 of Day-4, GnRH-MSD Animal Health (21 µg) was injected to a 7 to 8 week-old female rat to synchronize a surrogate. After checking vaginal plug in a surrogate on Day 1, a surrogate suitable for transplant of fertilized egg was selected. On Day-0, the surrogate was allowed to mate a male rat which already has a vasectomy. From the fertilized eggs cultured for a day, only the eggs grown to 2-cell level were selected and transplanted to oviduct ampulla of the surrogate. When a pregnant surrogate gives birth to a cloned baby rat, ear of the baby rat was cut off and subjected to genotyping to determine the traits of animal.

5. F9 Rat-Targeting Deep Sequencing (Genotype Analysis)

Around the weaning period of the cloned baby rat obtained from the pregnant surrogate (i.e., 3 week-old baby rat), the rat ear was cut off and gDNA was extracted from the ear to determine the traits of animal. By using Phusion polymerase taq (New England BioLabs) for the ear of transfected rat, PCR amplification was carried out with use of the on-target part. After that, the amplified product of PCR was subjected to Paired-end deep sequencing using Mi-Seq (Illumina). Results of the deep sequencing were analyzed by Cas-Analyzer tool (www.rgenome.net).

PCR primers
Forward:
                                    (SEQ ID NO: 36)
ACACTCTTTCCCTACACGACGCTCTTCCGATCTCGTCCAAAGAGATATAA

CTCAGG

Reverse:
                                    (SEQ ID NO: 14)
GTGACTGGAGTTCAGACGTGTGCTCTTCCGATCTTCGTGCTTCTTCAAAA

CTGC

6. Serological Analysis of F9 Rat

Figure 1B:
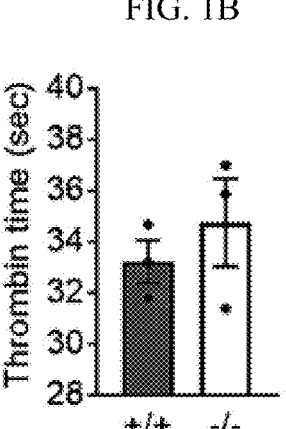
Figure 1C:
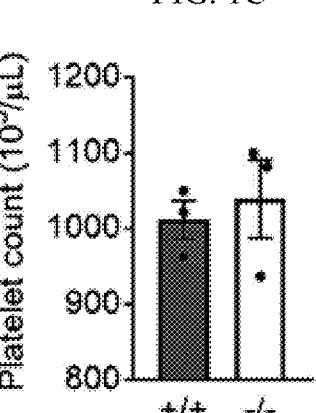

After the trait analysis of F9, 10 to 13 week-old (F1 generation) rat was anesthetized and blood was taken from the abdominal arteries. Then, the blood was collected by using SST-BD (serum separated) tube and incubated for an hour at room temperature followed by centrifugation for 15 minutes at 3000 rpm using centrifuge to separate serum. The separated serum was sent to Green Cross Labs to have a serological test. A screening test for evaluating the function of coagulation factors (F-viii, ix, xi, xii) involved in intrinsic system, extrinsic system, i.e., PTT (prothrombin time), and, as a method of directly measuring the activity of fibrinogen, a method of analyzing the time taken to form increased clot as fibrinogen turns into fibrin according to addition of thrombin to platelet-poor plasma, i.e., TT (thrombin time), were analyzed (see, FIG. 1B). For the 16 week-old rat (F1 generation), analysis was made for the platelet as a factor involved in the mechanism of hemostasis, which is one of the type components present in peripheral blood.

7. Histological Analysis of F9 Rat

Figure 3A:
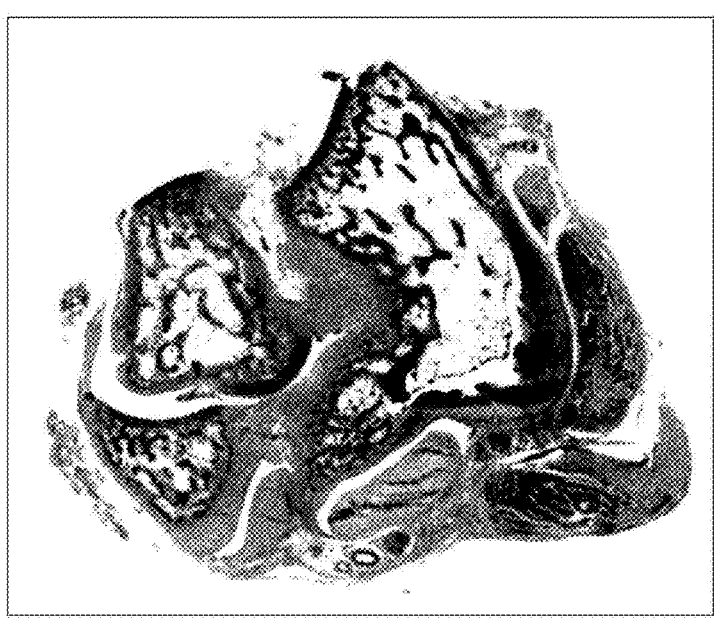
FIGS. 3A and 3B are photographic images illustrating the result of observing the pain region of a F9 rat after excising only the pain region and subjecting it to hematoxylin and eosin (H&E) staining to determine the morphology of the pain region of a F9 rat.
Figure 3B:
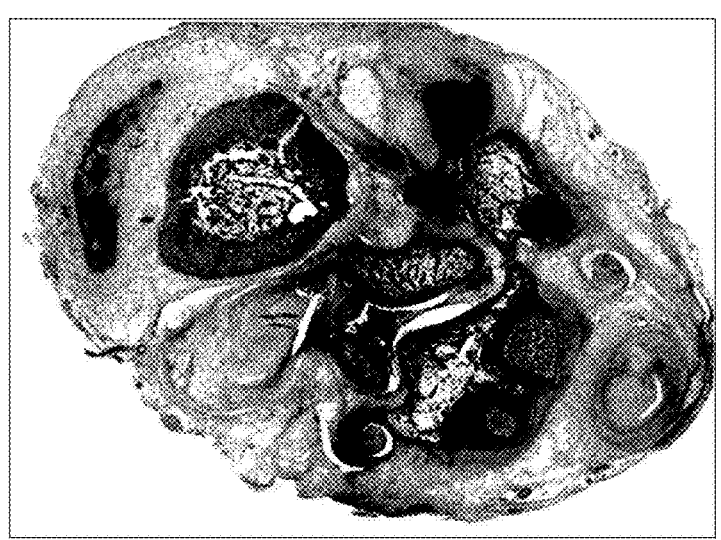
Figure 8:
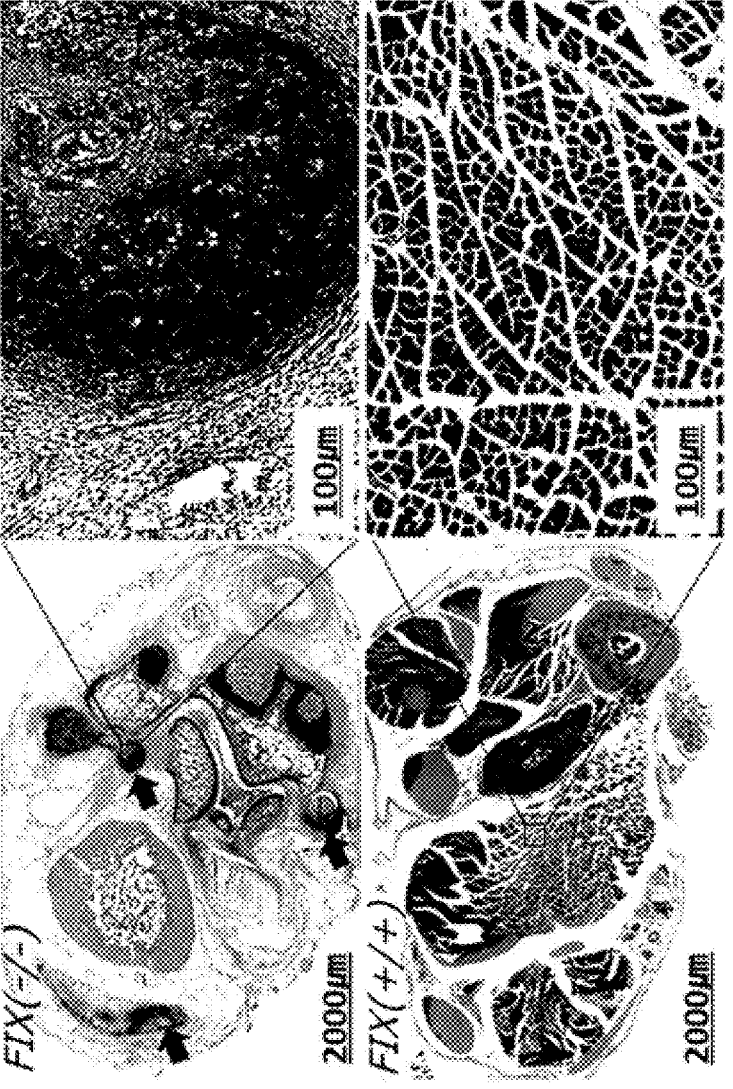
FIG. 8 is a photographic image illustrating the result of observing a histological change in the femoral muscles of F9(+/+) rat and F9(−/−) rat after performing hematoxylin and eosin (H&E) staining.

In order to observe a histological change in femoral tissues of F9 rat, hematoxylin and eosin staining (H&E staining) was carried out. For example, FIGS. 3A and 3B are photographic images illustrating the result of observing the pain region of a F9 rat after excising only the pain region and subjecting it to hematoxylin and eosin (H&E) staining to determine the morphology of the pain region of a F9 rat. After deparaffinization of formalin-fixed and paraffin-embedded tissue section in xylene, the tissue section was rehydrated with absolute alcohol. After brief wash with tap water, the tissue section was stained for 5 minutes with Harris hematoxylin. Slide was rinsed for 5 minutes with tap water and stained for 30 seconds in 0.2% ammonia water. After washing for 5 minutes with tap water, the slide was impregnated for 2 minutes and 30 seconds in Y eosin. After that, the slide was dehydrated 2 times with 95% alcohol and washed 2 times with xylene. Finally, a cover slip was applied with xylene-based medium followed by observation. Results obtained from the observation are illustrated in FIG. 8.

8. Histopathological Analysis of F9 Rat

To determine the morphology of a site of pain via H&E staining, only the area showing pain in F9 rat was cut out and added to 4% paraformaldehyde followed by fixing and washing steps. After that, a paraffin block was prepared, cut (10 μm), and attached to a slide. As a rehydration step, paraffin in the tissues attached to paraffin were dissolved first by using xylene so as to create a condition for staining. As a staining step, the nucleus was stained with Harris hematoxylin and the cytoplasm was stained with eosin. Harris hematoxylin exhibits blue color while eosin exhibits red color. As a final step, dehydration was carried out so that the staining can be maintained without any change.

9. Analysis of Bleeding from F9 Rat

Figure 2:
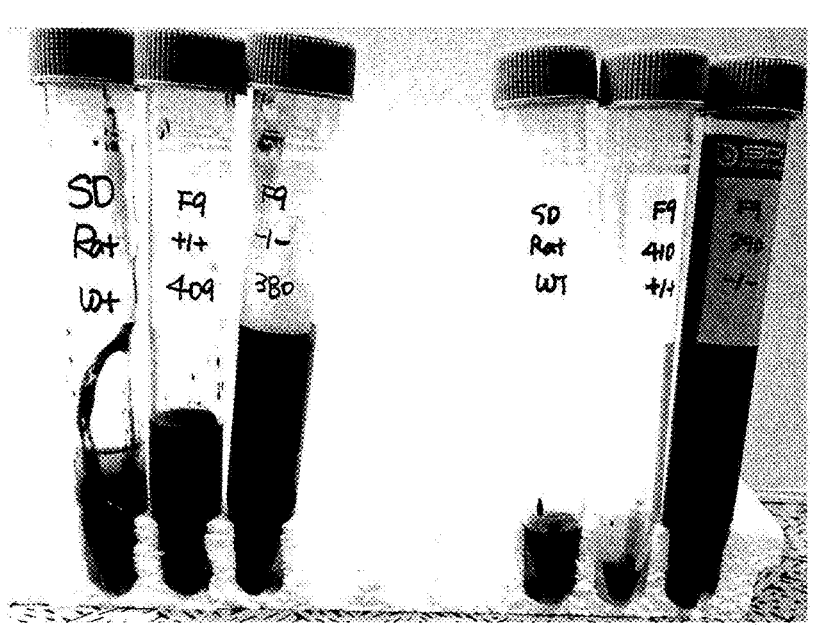
FIG. 2 is a photographic image comparing the bleeding amount of F9(+/+) rats and F9(−/−) rats for 10 minutes after tail cutting at the same time.

Bleeding analysis was carried out by using 16 week-old control group (F1 generation), F9+/+, and F9−/− (see, FIG. 2). First, the animal was anesthetized and a 15 ml tube for collecting blood was fixed under the tail to collect the blood loss by the animal bleeding. Tails of three rats were cut off simultaneously and the time was measured using a stopwatch. Furthermore, video recording was carried out to determine the real-time bleeding amount.

The present specification provides a hemophilia B rat and a method of producing the hemophilia B rat. As an animal model for human hemophilia B, the rat animal model can sufficiently exhibit the symptoms of hemophilia B, more particularly, the symptoms of spontaneous bleeding, and thus it can provide an important tool for developing therapeutic agents in future.

Furthermore, to produce a hemophilia B rat, a composition for engineering F9 gene to produce a hemophilia B rate model is provided according to the present application, and it can be used for producing a hemophilia B rat.

---

What is claimed is:

1. A hemophilia B rat model comprising artificial modification in F9 gene, wherein the artificial modification in F9 gene comprises one or more modifications of:

a deletion of a whole or partial sequence of F9 gene;

an insertion in a whole or partial sequence of F9 gene;

an insertion and deletion of a whole or partial sequence of F9 gene; and an inversion in F9 gene, wherein the partial sequence of F9 gene is a 1 bp to 100 bp nucleotides, wherein the hemophilia B rat comprises, thereby the artificial modification in F9 gene, one or more of:

a reduced expression level of F9 factor;

an inhibited expression of F9 factor;

a hypofunction of F9 factor; and a lost function of F9 factor, and wherein the hemophilia B rat exhibits one or more phenomena of:

a spontaneous bleeding in tissues;

an inflammation in tissues caused by spontaneous bleeding; and a swelling in tissues caused by spontaneous bleeding, wherein the artificial modification in F9 gene occurs in the second exon region of F9 gene.

* * * * *